United States Patent
Hansen et al.

(10) Patent No.: US 11,478,476 B2
(45) Date of Patent: Oct. 25, 2022

(54) USE OF BUSPIRONE METABOLITES

(71) Applicant: CONTERA PHARMA APS, Copenhagen (DK)

(72) Inventors: John Bondo Hansen, Copenhagen (DK); Mikael S. Thomsen, Hvidovre (DK)

(73) Assignee: CONTERA PHARMA APS, Copenhagen (DK)

( * ) Notice: Subject to any disclaimer, the term of this patent is extended or adjusted under 35 U.S.C. 154(b) by 185 days.

(21) Appl. No.: 15/318,518

(22) PCT Filed: Jun. 25, 2015

(86) PCT No.: PCT/DK2015/050186
§ 371 (c)(1),
(2) Date: Dec. 13, 2016

(87) PCT Pub. No.: WO2015/197079
PCT Pub. Date: Dec. 30, 2015

(65) Prior Publication Data
US 2017/0128446 A1 May 11, 2017

(30) Foreign Application Priority Data

Jun. 26, 2014 (DK) .............. PA 2014 70388
Jun. 26, 2014 (DK) .............. PA 2014 70389

(Continued)

(51) Int. Cl.
A61K 31/506 (2006.01)
A61K 31/422 (2006.01)
(Continued)

(52) U.S. Cl.
CPC .......... *A61K 31/506* (2013.01); *A61K 31/198* (2013.01); *A61K 31/4166* (2013.01);
(Continued)

(58) Field of Classification Search
CPC ... A61K 31/506; A61K 31/422; A61K 31/423
(Continued)

(56) References Cited

U.S. PATENT DOCUMENTS 4,438,119 A * 3/1984 Allen .................. A61K 31/505
514/252.15
5,866,585 A * 2/1999 Fogel .................... A61K 31/00
514/289

(Continued)

FOREIGN PATENT DOCUMENTS

EP 1047436 B1 * 10/2009 ............ A61K 31/00
JP 2002-509104 A 3/2002
(Continued)

OTHER PUBLICATIONS

Moss et al, (1993) "Buspirone in the treatment of Tardive Dyskinesia.", J. Clin. Psychopharmacol 13(3):204-209. (Year: 1993).*
(Continued)

*Primary Examiner* — Craig D Ricci
*Assistant Examiner* — Janet L Coppins
(74) *Attorney, Agent, or Firm* — Harness, Dickey & Pierce, P.L.C.

(57) ABSTRACT

The present invention is directed to a composition comprising a buspirone metabolite, alone or in combination with a second active ingredient, for use in the treatment of movement disorders.

11 Claims, 2 Drawing Sheets

(30) Foreign Application Priority Data

Feb. 26, 2015 (DK) .......................... PA 2015 70101
Feb. 26, 2015 (DK) .......................... PA 2015 70102

(51) Int. Cl.
| | |
|---|---|
| A61K 45/06 | (2006.01) |
| A61K 31/4196 | (2006.01) |
| A61K 31/423 | (2006.01) |
| A61K 31/7048 | (2006.01) |
| A61K 31/4166 | (2006.01) |
| A61K 31/198 | (2006.01) |
| A61K 31/4168 | (2006.01) |

(52) U.S. Cl.
CPC ...... *A61K 31/4168* (2013.01); *A61K 31/4196* (2013.01); *A61K 31/422* (2013.01); *A61K 31/423* (2013.01); *A61K 31/7048* (2013.01); *A61K 45/06* (2013.01)

(58) Field of Classification Search
USPC .................................................. 514/252.15
See application file for complete search history.

(56) References Cited

U.S. PATENT DOCUMENTS

| | | | | |
|---|---|---|---|---|
| 6,686,361 | B2* | 2/2004 | Yevich | C07D 401/12 514/252.15 |
| 2002/0193380 | A1 | 12/2002 | Camborde et al. | |
| 2003/0022899 | A1* | 1/2003 | Yevich | A61K 31/506 514/252.15 |
| 2003/0055063 | A1 | 3/2003 | Yevich et al. | |
| 2005/0137206 | A1 | 6/2005 | Yevich et al. | |
| 2013/0252965 | A1* | 9/2013 | Hansen | A61K 31/422 514/252.15 |

FOREIGN PATENT DOCUMENTS

| | | | | |
|---|---|---|---|---|
| JP | 2003-520236 A | 7/2003 | | |
| WO | WO-9313766 A1 * | 7/1993 | ........... | A61K 31/335 |
| WO | WO-99/36064 A2 | 7/1999 | | |
| WO | WO-01/52853 A1 | 7/2001 | | |
| WO | WO 2003/009851 | 2/2003 | ........... | A61K 31/506 |
| WO | WO 03009851 A1 * | 2/2003 | ........... | C07D 401/12 |
| WO | WO-03009851 A1 * | 2/2003 | ........... | C07D 401/12 |
| WO | WO 2009/156380 | 12/2009 | ........... | A61K 31/198 |
| WO | WO 2012/048710 | 4/2012 | ........... | A61K 31/422 |
| WO | WO 2013/156035 | 10/2013 | ............... | A61K 9/22 |

OTHER PUBLICATIONS

Wong et al, (2007) "6-Hydroxybuspirone Is a Major Active Metabolite of Buspirone: Assessment of Pharmacokinetics and 5-Hydroxytryptamine1 A Receptor Occupancy in Rats.", Drua Metabolism and Disposition, 35(8):1387-1392. (Year: 2007).*

Moss et al, (1993) "Buspirone in the treatment of Tardive Dyskinesia.", J. Clin. Psychopharmacol13(3):204-209. (Year: 1993).*

Wong et al, (2007) "6-Hydroxybuspirone Is a Major Active Metabolite of Buspirone: Assessment of Pharmacokinetics and 5-Hydroxytryptamine1 A Receptor Occupancy in Rats.", Drua Metabolism and Disposition, 35(8):1387-1392. (Year: 2007).*

Bergman, J., et al. (2013) "Modification of cocaine self-administration by buspirone (buspar1): potential involvement of D3 and D4 dopamine receptors.", *International Journal of Neuropsychopharmacology*, 16:445-458.

Bonifati, V., et al. (1994) "Buspirone in Levodopa-induced Dyskinesias.", *Clinical Neuropharmacology*, 17(1):73-82.

Creed, M., et al. (2012) "Contribution of decreased serotonin release to the antidyskinetic effects of deep brain stimulation in a rodent model of tardive dyskinesia: comparison of the subthalamic and entopeduncular nuclei.", *The Journal of Neuroscience*, 32(28):9574-9581.

Dockens, R., et al. (2007) "Pharmacokinetics of 6-hydroxybuspirone and its enantiomers administered individually or following buspirone administration in humans.", *Biopharmaceutics & Drug Disposition*, 28(7):393-402, XP002744117, ISSN: 0142-2782.

Eskow, K., et al. (2007) "The partial 5-HT1A agonist buspirone reduces the expression and development of l-DOPA-induced dyskinesia in rats and improves l-DOPA efficacy.", *Pharmacology, Biochemistry and Behavior*, 87:306-314.

Gammans, R., et al. (1986) "Metabolism and disposition of buspirone.", *The American Journal of Medicine*, 80(suppl 3B):41-51.

Gregoire, L., et al. (2009) "Low doses of sarizotan reduce dyskinesias and maintain antiparkinsonian efficacy of L-Dopa in parkinsonian monkeys.", *Parkinsonism and Related Disorders* 15:445-452.

Hout, P., et al. (2011) "Anatomically selective serotonergic type 1a and serotonergic type 2a therapies for parkinson's disease: an approach to reducing dyskinesia without exacerbating parkinsonism?", *The Journal of Pharmacology and Experimental Therapeutics*, 339(1):2-8.

Hout, P., et al. (2012) "L-745,870 Reduces L-DOPA-Induced Dyskinesia in the 1-Methyl-4-Phenyl-1,2,3,6-Tetrahydropyridine-Lesioned Macaque Model of Parkinson's Disease.", *The Journal of Pharmacology and Experimental Therapeutics*, 342(2): 576-585.

Hout, P., et al. (2013) "The Pharmacology of L-DOPA-Induced Dyskinesia in Parkinson's Disease.", *Pharmacological Reviews*, 65:171-222.

Jankelowitz, S., et al. (2013) "Treatment of neurolept-induced tardive dyskinesia.", *Neuropsychiatric Disease and Treatment*, 9:1371-1380.

Kim, J., et al. (2014) "Tardive dyskinesia in patients treated with atypical antipsychotics: case series and brief review of etiologic and treatment considerations.", *Drugs in Context, The Journal of Interventions in Clinical Practice*, 3:212259. doi: 10.7573/dic.212259.

Kim, S W., et al. (2014) "Therapeutic doses of buspirone block D3 receptors in the living primate brain.", *International Journal of Neuropsychopharmacology*, pp. 1-11.

Kirik, D., et al., (2001) "Growth and Functional Efficacy of Intrastriatal Nigral Transplants Depend on the Extent of Nigrosthatal Degeneration.", *The Journal of Neuroscience*, 21(8):2889-2896.

Kleedorfer, B., et al. (1991) "Buspirone in the treatment of levodopa induced dyskinesias.", *J. Neurol. Neurosurg. Psychiatry*, 54:376-377 doi:10.1136/jnnp.54.4.376-a.

Lindenbach, D., et al. (2014) "Side effect profile of 5-HT treatments for Parkinson's disease and L-DOPA-induced dyskinesia in rats." *British Journal of Pharmacology*, 172:119-130.

Ludwig, C., et al. (1986) "Buspirone, Parkinson's Disease, and the Locus Ceruleus.", *Clinical Neuropharmacology*, 9(4):373-378.

Manahan-Vaughan, D., et al. (1995) "The azapirone metabolite 1-(2-pyrimidinyl)piperazine depresses excitatory synaptic transmission in the hippocampus of the alert rat via 5-HTIA receptors.", *European Journal of Pharmacology*, 294:617-624.

Moss, L., et al. (1993) "Buspirone in the treatment of Tardive Dyskinesia.", *J. Clin. Psychopharmacol.*, 13(3):204-209.

Munoz, A., et al., (2008) "Combined 5-HT1A and 5-HT1B receptor agonists for the treatment of L-DOPA-induced dyskinesia.", *Brain*, 131:3380-3394.

Munoz, A., et al., (2009) "Serotonin neuron-dependent and -independent reduction of dyskinesia by 5-HT1A and 5-HT1B receptor agonists in the rat Parkinson model.", *Experimental Neurology*, 219:298-307.

Naidu, P., et al. (2001) "Effect of 5-HT and 5-HT receptor modulation on 1A 2Ar2C neuroleptic-induced vacuous chewing movements.", *European Journal of Pharmacology*, 428:81-86.

Rosengarten, H., et al. (2006) "The effect of chronic administration of sarizotan, 5-HT1A agonist/D3/D4 ligand, on haloperidol-induced repetitive jaw movements in rat model of tardive dyskinesia.", *Progress in Neuro-Psychopharmacology & Biological Psychiatry*, 30:273-279.

Schallert, T., et al., (1992) "A Clinically Relevant Unilateral Rat Model of Parkinsonian Akinesia.", *Journal of Neural Transplantation & Plasticity*, 3(4):332-333.

Wong, H., et al. (2007) "6-Hydroxybuspirone Is a Major Active Metabolite of Buspirone: Assessment of Pharmacokinetics and

(56) References Cited

OTHER PUBLICATIONS

5-Hydroxytryptamine1A Receptor Occupancy in Rats.", *Drug Metabolism and Disposition*, 35(8):1387-1392.

Wulff, H., et al., (2009) "Voltage-gated Potassium Channels as Therapeutic Drug Targets.", *Nat Rev Drug Discov.*, 8(12):982-1001, doi:10.1038/nrd2983.

Xiong, Q., et al., (2008) "Activation of Kv7 (KCNQ) voltage-gated potassium channels by synthetic compounds.", *Trends in Pharmacological Sciences*, 29(2):99-107.

Zhu, M., et al., (2005). "Cytochrome P450 3A-mediated metabolism of buspirone in human liver microsomes". *Drug Metabolism and Disposition*, 33(4):500-507, XP002744118, ISSN: 0090-9556.

International Search Report (ISR) dated Nov. 23, 2015 in PCT/DK2015/050186 published as WO 2015/197079.

Egan, M. F., et al.; "Treatment of Tardive Dyskinesia", Schizophrenia Bulletin, 1997, vol. 23, No. 4, pp. 583-609.

\* cited by examiner

Buspirone

6-OH Buspirone

USE OF BUSPIRONE METABOLITES

CROSS-REFERENCE TO RELATED APPLICATIONS

This application is a national phase application of PCT Application No. PCT/DK2015/050186, filed on Jun. 25, 2015, which claims priority to PA 2015 70102 and PA 2015 70101 filed 26 Feb. 2015 and PA 2014 70388 and PA 2014 70389, filed 26 Jun. 2014. The entire disclosure of the applications identified in this paragraph is incorporated herein by reference.

FIELD OF INVENTION

The present invention relates to a composition comprising a buspirone metabolite, in particular 6-hydroxy buspirone, for use in the treatment of movement disorders. The buspirone metabolites may be used alone or in combination with other compounds such as compounds used for treatment of said movement disorders.

BACKGROUND OF INVENTION

Movement disorders are a group of diseases that affect the ability to produce and control body movement, and are often associated with neurological disorders or conditions associated with neurological dysfunction. Movement disorders may manifest themselves in abnormal fluency or speed of movement, excessive or involuntary movement, or slowed or absent voluntary movement.

Movement disorders are frequently caused by impaired regulation of dopamine neurotransmission. Parkinson's disease (PD) is an example of a movement disorder associated with dysfunctional regulation of dopamine neurotransmission, which is caused by progressive degeneration of dopamine neurons. Tardive dyskinesia is another example of a movement disorder associated with dysfunctional regulation of dopamine neurotransmission.

In order to replace the lost dopamine, PD is currently treated with e.g. levodopa (L-DOPA, a precursor of dopamine). Unfortunately, the treatment of PD with L-DOPA often gives rise to a specific type of dyskinesia called L-DOPA Induced Dyskinesia (LID) which, in part, is caused by excessive dopamine levels in the synapses.

Dopamine release and re-uptake is regulated by a number of neurotransmitters, including serotonin (5-HT). Serotonin acts by binding to a number of different serotonergic receptors, of which agonists and antagonists of some serotonergic receptors have been investigated for treatment of movement disorders.

Modulators of serotonin (5-HT) neurotransmission individually have been shown to ameliorate or prevent LID. One example thereof is sarizotan, which is a 5-HT1A agonist and a dopamine receptor antagonist (Grégoire et al: *Parkinsonism Relat Disord.* 2009; 15(6): 445-52). In pre-clinical and clinical studies sarizotan reduced LID, however, in phase 2b and 3 studies no significant effects of sarizotan compared to placebo could be shown. Sarizotan has also been shown to have effects in a pre-clinical model of tardive dyskinesia (Rosegarten et al: Progress in Neuro-Psychopharmacology & Biological Psychiatry 30 (2006) 273-279). A selective antagonist of dopamine D4 receptors also reduced LID in a non-human primate model (P. Huot et al: JPET 342:576-585, 2012).

Buspirone and 5-HT1A agonists in general have been shown to reduce abnormal involuntary movements associated with L-DOPA treatment of Parkinson's disease (L-DOPA induced dyskinesia, LID) (for a review see e.g. P. Huot at al: Pharmacol Rev 65:171-222, 2013) and tardive dyskinesia (TD) associated with neuroleptic treatment of schizophrenia (e.g. Naidu et al: Eur J Pharmacol. 2001, 28; 428(1): 81-6; Creed et al: The Journal of Neuroscience, 2012, 32(28): 9574-9581.

The effects of the 5-HT1A agonist buspirone on Parkinson's disease have been studied in a small open study (Ludwig et al: Clin Neuropharmacol. 1986; 9(4):373-8). It was found that doses (10-60 mg/day), which are normally used to treat patients suffering from anxiety, did not have any effects on Parkinson's disease or dyskinesia. At higher doses (100 mg/day) it was observed that buspirone reduced dyskinesia but with a significant worsening of disability ratings. This showed that high doses of buspirone could worsen the akinesia associated with Parkinson's disease. Other studies have shown that buspirone reduce L-DOPA induced dyskinesia in exploratory clinical studies (Bonifati et. al., 1994, Kleedorfer et al., 1991). Buspirone has furthermore been shown to have effects in clinical studies in tardive dyskinesia (Moss et. al., 1993).

5-HT1A agonists given in high doses can lead to the development of the serotonin syndrome or serotonin toxicity; a form of poisoning. Because of the severity of serotonin syndrome, it is therefore important to maintain a low exposure of the 5-HT1A agonist.

The serotonin syndrome is caused by increased activation of the 5-HT1A and 5-HT2A receptors. Serotonin syndrome, by definition, is a group of symptoms presenting as mental changes, autonomic nervous system malfunction, and neuromuscular complaints. Patients may present with confusion, agitation, diarrhoea, sweating, shivering, hypertension, fever, increased white blood cell count, incoordination, marked increase in reflexes, muscle jerks, tremor, extreme stiffness, seizures and even coma. The severity of changes ranges from mild to fatal.

In order to increase efficacy of 5-HT1A agonists in reducing LID in animal models a combination of a 5-HT1A and a 5-HT1B agonist has been tested (e.g. Muñoz et al: *Brain.* 2008; 131: 3380-94; Muñoz et al: *Experimental Neurology* 219 (2009) 298-307). The combined 5-HT1A and 5-HT1B agonist eltoprazine has also been suggested for treatment of LID (WO2009/156380) as well as an agonist of two or more the 5-HT1B, 5-HT1D and 5-HT1F receptors in combination with a 5-HT1A agonist when assayed in an animal model for LID, thus effectively increasing the therapeutic index (WO2012/048710).

Orally administrated buspirone undergoes extensive first pass metabolism, which limits bioavailability of the parent compound (4% in humans). This potentially will reduce the duration of action of the compound and necessitate the use of higher or multiple doses. Buspirone is metabolized through cytochrome P450 enzymes. This will potentially increase the risk of drug-drug interactions, which is particularly relevant for patients with movement disorders who often receive more than one medicament.

SUMMARY OF INVENTION

The present inventors have surprisingly found that metabolites of buspirone are able to reduce abnormal involuntary movements associated with certain movement disorders and that beneficial effects of the metabolites of buspirone can be potentiated by drugs affecting central neurotransmitter activity. The metabolites of buspirone alone or in combination with other drugs that actively affect central neurotransmitter activity will effectively influence the neurotransmitter levels in the brain that are important for normal motor function. The finding is useful in the treatment of diseases associated with altered or impaired synaptic dopamine levels such as movement disorders including for example L-DOPA induced dyskinesia and tardive dyskinesia.

It is an aspect of the present invention to provide a pharmaceutical composition or kit of parts comprising a buspirone metabolite, or a pharmaceutically acceptable derivative thereof, for use in the treatment, prevention or alleviation of movement disorders.

In one embodiment said buspirone metabolite is selected from the group consisting of 6-OH-Busp, Oxa-Busp, 3-OH-Busp, 5-OH-Busp, 5,6-di-OH-Busp, Busp N-oxide, 5-OH-1-PP and 1-PP; including the racemates, the S-forms and/or the R-forms thereof.

In one embodiment said composition further comprises a second active ingredient. Combining a buspirone metabolite and a second active ingredient according to the present invention in one embodiment provides an additive or synergistic effect compared to use of the buspirone metabolite itself; and/or potentiates the therapeutic effect of one or both of each ingredient when compared to use of either ingredient alone.

In one embodiment the second active ingredient is an agonist of two or more of the 5-HT1B, 5-HT1D and 5-HT1F receptors, such as a triptan, a selective 5-HT1B receptor agonist, a selective 5-HT1D receptor agonist, a selective 5-HT1E receptor agonist or a selective 5-HT1F receptor agonist.

In one embodiment the second active ingredient is a modulator of glutamate neurotransmission, a glutamate receptor antagonist, a NMDA receptor antagonist, an AMPA receptor antagonist, a kainite receptor antagonist, an AMPAR/kainite receptor antagonist, an mGluR Group 1 antagonist, an mGluR Group 2 agonist, an mGluR Group 3 agonist, and an inhibitor of presynaptic glutamate release.

In one embodiment the second active ingredient is an ion-channel antagonist, such as a T-Type calcium channel antagonist, an L-Type calcium channels antagonist, a K$^+$ channel antagonist and/or a Na$^+$ channel antagonist; or a KCNQ channel modulator.

In one embodiment the composition of the present invention, comprising a buspirone metabolite and optionally a second active ingredient further comprises one or more further active ingredients, such as agents which are used for treatment of the relevant movement disorder, such as Parkinson's disease.

In one embodiment the movement disorder of the present invention is a movement disorder associated with altered or impaired synaptic dopamine levels; Parkinson's disease; movement disorders associated with Parkinson's disease such as bradykinesia, akinesia and dyskinesia; L-DOPA induced dyskinesia (LID); tardive dyskinesia and akathisia.

Definitions

The term "agonist" in the present context refers to a substance capable of binding to and activating a (one or more) receptor(s). A 5-HT1A receptor agonist (5-HT1A agonist) is thus capable of binding to and activating the 5-HT1A receptor. An agonist of two or more the 5-HT1B, 5-HT1D and 5-HT1F receptors (5-HT1B/D/F agonist) is capable of binding to and activating two or three of the 5-HT1B, 5-HT1D and 5-HT1F receptors. The terms '5-HT1 agonist', '5-HT1 receptor agonist', and 'agonist of the 5-HT1 receptor' are used interchangeably herein.

The term "antagonist" in the present context refers to a substance capable of inhibiting the effect of a receptor agonist.

"Partial agonists" in the present context are compounds able to bind and activate a given receptor, but having only partial efficacy at the receptor relative to a "full agonist". Partial agonists can act as antagonists when competing with a full agonist for receptor occupancy and producing a net decrease in the receptor activation compared to the effects or activation observed with the full agonist alone.

"Selective agonists" in the present context are compounds which are selective and therefore predominantly bind and activate one type of receptor. Thus a selective 5-HT1A receptor agonist is selective for the 5-HT1A receptor, a selective 5-HT1B receptor agonist is selective for the 5-HT1B receptor, a selective 5-HT1D receptor agonist is selective for the 5-HT1D receptor, and a selective 5-HT1F receptor agonist is selective for the 5-HT1F receptor.

"Allosteric modulators" in the present context are compounds, which indirectly influences (modulates) the effects of an agonist or inverse agonist at a target protein, for example a receptor. Allosteric modulators bind to a site distinct from that of the orthosteric agonist binding site. Usually they induce a conformational change within the protein structure. A positive allosteric modulator (PAM), which is also called an allosteric enhancer, induces an amplification of the agonists' effect. A negative allosteric modulator (NAM) reduces the effects of the orthosteric ligand, but is inactive in the absence of the orthosteric ligand.

An inverse agonist is an agent that binds to the same constitutively active receptor as an agonist but induces a pharmacological response opposite to that agonist. A neutral antagonist has no activity in the absence of an agonist or inverse agonist but can block the activity of either.

The terms "dopamine," "DA" and "4-(2-aminoethyl)benzene-1,2-diol," refer to a catecholamine neurotransmitter and hormone. Dopamine is a precursor of adrenaline (epinephrine) and noradrenaline (norepinephrine) and activates the five types of dopamine receptors—D1, D2, D3, D4, and D5—and their variants.

"L-DOPA" or "3,4-dihydroxyphenylalanine" is a precursor to the neurotransmitters dopamine, norepinephrine (noradrenaline), and epinephrine (adrenaline). L-DOPA is able to cross the blood-brain barrier, and is converted to dopamine by the enzyme aromatic L-amino acid decarboxylase (AADC), also known as DOPA decarboxylase (DDC). L-DOPA is used for treatment of Parkinson's disease.

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

The term "therapeutically effective amount" of a compound as used herein refers to an amount sufficient to cure, alleviate, prevent, reduce the risk of, or partially arrest the clinical manifestations of a given disease or disorder and its complications.

The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The patient to be treated is preferably a mammal, in particular a human being.

DETAILED DESCRIPTION OF THE INVENTION

The present invention is directed to use of a buspirone metabolite for treatment of movement disorders.

In order to avoid the risk of serotonin syndrome and the worsening of disability ratings associated with higher doses of buspirone the present invention provides a solution that addresses the need to maintain a low exposure of buspirone while maintaining clinically relevant efficacy.

Provision of a buspirone metabolite for treatment of movement disorders will enable a higher exposure per dosage and simultaneously reduce the risk of drug-drug-interactions.

The effect of buspirone on movement disorders has been documented, which effect is likely mediated by buspirone per se in combination with its metabolites. The extent to which the parent compound and the individual metabolites contribute to the effects of buspirone for a given condition is unknown.

Buspirone and its Metabolites

Buspirone (8-[4-(4-pyrimidin-2-ylpiperazin-1-yl)butyl]-8-azaspiro[4.5]decane-7,9-dione) is a drug of the azapirone chemical class approved for treatment of anxiety disorders. Buspirone is a serotonin 5-HT1A receptor partial agonist, which is thought to mediate its anxiolytic and antidepressant effects. Additionally, it is a presynaptic dopamine antagonist at the D2, D3 and D4 receptors, and a partial $\alpha_1$ receptor agonist.

Buspirone is in vivo rapidly metabolised to e.g. 6-hydroxybuspirone (6-OH-Busp; 6-hydroxy-8-[4[4-(2-pyrimidinyl)1-piperazinyl]butyl-8-azaspiro(4,5)-decane-7,9-dione; M6), which metabolites affect 5-HT1A receptors in a similar manner albeit slightly less potent than the parent compound. 6-OH-Busp is also an antagonist of dopamine D4 receptors with affinity in the same order of magnitude as for 5-HT1A receptors.

The effects of 6-OH-Busp (as racemate or purified enantiomers) in preclinical models of anxiety and depression (US 2005/0137206; US 2003/0055063; US 2003/0022899); and pain in combination with paracetamol (US 2002/0193380) have been described. In these studies 6-OH-Busp is active after IP and SC administration at doses that did not cause sedation.

Metabolism of Buspirone

Figure 1:
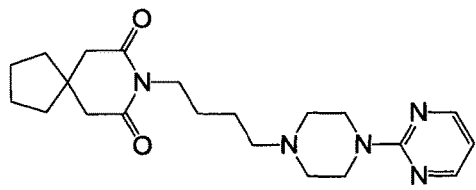
FIG. 1: Buspirone (8-[4-(4-pyrimidin-2-ylpiperazin-1-yl) butyl]-8-azaspiro[4.5]decane-7,9-dione) and its metabolite 6-hydroxybuspirone (6-OH-Busp; 6-hydroxy-8-[4[4-(2-pyrimidinyl)1-piperazinyl]butyl-8-azaspiro(4,5)-decane-7,9-dione).
Figure 1:
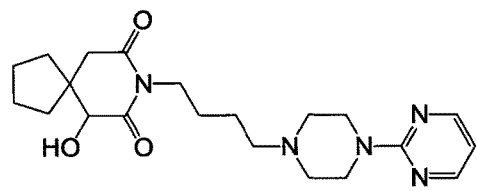
Figure 2:
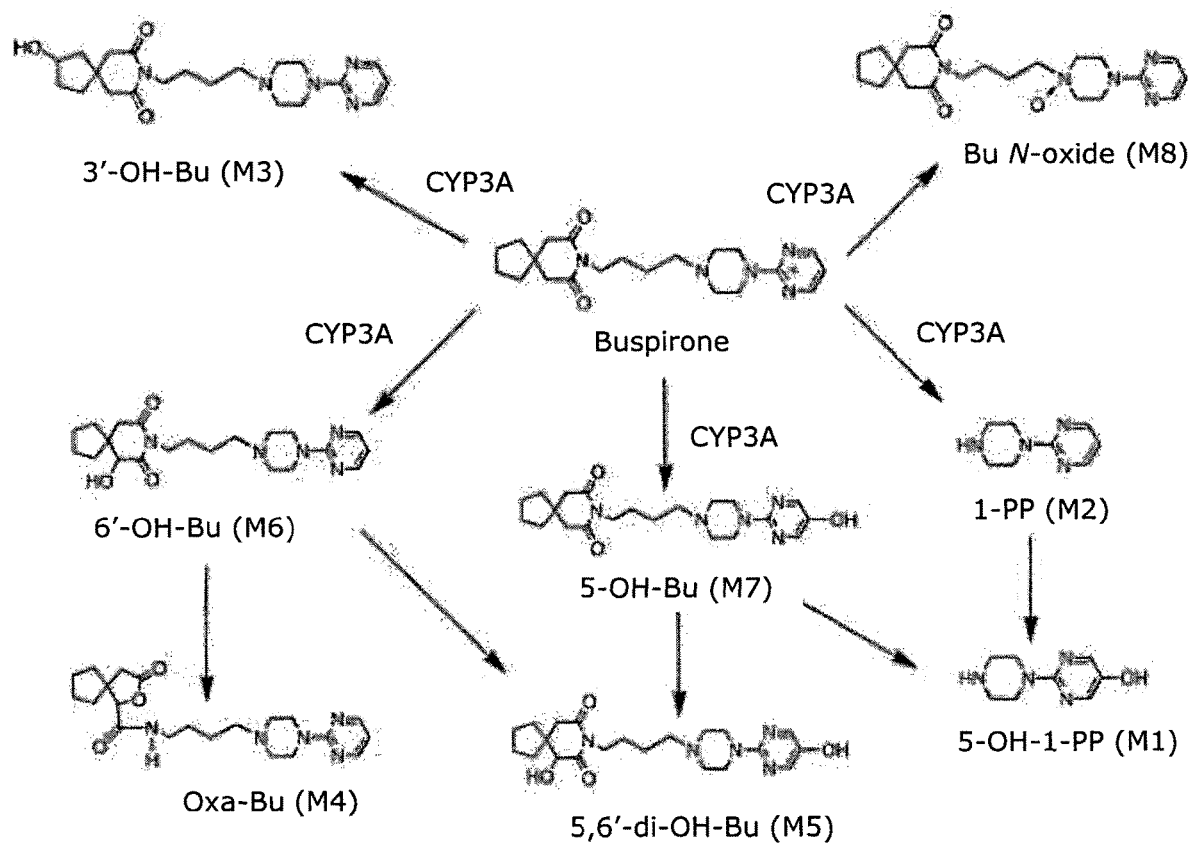
FIG. 2: Metabolic pathways of buspirone in human liver microsomes. The primary P450 enzyme responsible for each of the major metabolic pathways in human liver microsomes is also listed (M. Zhu et al: Drug Metabolism Disposition, 33:500-507, 2005).

Buspirone undergoes extensive first-pass metabolism in humans, resulting in a bioavailability of less than 5%. Unchanged buspirone accounts for less than 2% of the total radioactivity in human plasma after administration of radiolabeled buspirone (Gammans et al: Am J Med 80, 41-51, 1986). The rodent and human metabolism of buspirone has been characterized (see e.g. Zhu et al: Drug Metabolism Disposition, 33:500-507, 2005) in vitro and in vivo. Overall the metabolism is identical in human and rat and results in formation of 1-pyrimidinylpiperazine (1-PP), 6-hydroxybuspirone (6-OH-Busp), 5-OH-Busp and multiple secondary metabolites (see FIG. 2 and table 1).

TABLE 1

| Metabolite | Alternative names |
| --- | --- |
| 6-OH-Busp | M6 |
|  | 6'-OH-Bu |
|  | 6-hydroxybuspirone |
|  | 6-hydroxy-8-[4[4-(2-pyrimidinyl)1-piperazinyl]butyl-8-azaspiro(4,5)-decane-7,9-dione |
| Oxa-Busp | M4 |
|  | Oxa-Bu, Oxa-Buspirone |
| 3-OH-Busp | M3 |
|  | 3'-OH-Bu, 3'-OH-Buspirone |
| 5-OH-Busp | M7 |
|  | 5-OH-Bu, 5-OH-Buspirone |
| 5,6-di-OH-Busp | M5 |
|  | 5,6'-di-OH-Bu, 5,6'-di-OH-Buspirone |
| Busp N-oxide | M8 |
|  | Bu N-oxide, Buspirone N-oxide |
| 5-OH-1-PP | M1 |
|  | 5-hydroxy-1-(2-pyrimidinyl)-piperazine |
| 1-PP | M2 |
|  | 1-(2-pyrimidinyl)-piperazine |

6-OH-Busp is the major metabolite formed through CYP3A4 (Cytochrome P450 3A4)-catalysed hydroxylation of buspirone. The CYP3A4 catalysed metabolism of buspirone potentially leads to increased risk of drug-drug-interactions. In vivo interactions have been observed between buspirone and e.g. itraconazole (triazole antifungal agent), rifampicin (bactericidal antibiotic drug), nefazodone (antidepressant), haloperidol (antipsychotic), carbamazepine (anticonvulsant and mood-stabilizing) and grapefruit.

The pharmacokinetic parameters of buspirone, racemic 6-OH-Busp and the R- and S-enantiomers of 6-OH-Busp after oral administration to human volunteers have been described (R. C. Dockens et al: Biopharm. Drug Dispos. 28: 393-402 (2007)). In this study it is shown that there is an inter-conversion between the enantiomers giving a preference for formation (or retention) of the S-form. Upon oral administration, buspirone is metabolised to 6-OH-Busp (both enantiomers) giving an exposure of parent compound, which is lower (Cmax: 1.39 ng/mL; $AUC_{0-INF\ (ngxh/ml)}$: 3.93) than total 6-OH-Busp (Cmax: 9.12 ng/mL; $AUC_{0-INF\ (ngxh/ml)}$: 52.93). Oral administration of racemic 6-OH-Busp in comparison gave much higher exposure of 6-OH-Busp (Cmax: 25.63 ng/mL; $AUC_{0-INF\ (ngxh/ml)}$: 131.52). The half-life (T½) of 6-OH-Busp is longer than that of buspirone, after administration of either parent buspirone or 6-OH-Busp, while there seems to be no significant difference in half-life between the two enantiomers.

Pharmacology of 6-OH-Busp—In Vitro

Several of the metabolites of buspirone have been characterized with respect to their affinity for central receptors (e.g. serotonin 5-HT1A and dopamine D2, D3, and D4 receptors). 6-OH-Busp is one of the most potent metabolites, which bind with high affinity to both 5-HT1A and dopamine D3 and D4 receptors. The affinity of buspirone and its metabolites to human recombinant 5-HT1A receptors have been described in US 2005/0137206. Table 2 below shows that buspirone has high affinity to 5-HT1A receptors in vitro (Ki=15 nM) and that 6-OH-Busp is slightly less potent (Ki=57 nM). Other metabolites of buspirone were less potent. The affinity of buspirone and 8-OH-DPAT for 5-HT1A receptors described here is in the same order of magnitude as described by others.

TABLE 2

| Compound | IC50 (nM) | STDEV | Ki | n |
|---|---|---|---|---|
| 8-OH-DPAT | 2.5 | 0.9 | 1 | 8 |
| Buspirone | 30 | 18 | 15 | 8 |
| 6-OH-Busp | 114 | 85 | 57 | 7 |
| 5-OH-Busp | 928 | 176 | 464 | 7 |
| 3-OH-Busp | 652 | 402 | 326 | 7 |
| 1-PP | >1000 | — | — | 3 |

6-OH-Busp is a racemate. The two enantiomers have been tested for effects on human recombinant 5-HT1A and dopamine D2 receptors in vitro and data is presented in U.S. Pat. No. 6,686,361 (table 3). The two enantiomers have similar affinity for the 5-HT1A receptor. Studies have shown that R- and S-forms racemize in vivo (see below).

TABLE 3

| | Buspirone Ki nM | 6-OH-Busp (S-form) Ki nM | 6-OH-Busp (R-form) Ki nM |
|---|---|---|---|
| 5-HT1A | 5 | 24 | 14 |
| D2 | 87 | 1300 | 2870 |

The effects of the major metabolites of buspirone on human recombinant dopamine (D2, D3 and D4) receptors have been determined by Bergman et al. (J. Bergman et al: International Journal of Neuropsychopharmacology (2013), 16, 445-458). The affinity of 6-OH-Busp to dopamine D4 is similar to that of buspirone and much stronger than the affinity to dopamine D3 and D2. The affinity for D4 is in the same order or slightly less than for 5-HT1AR. The efficacy of buspirone and its metabolites for the dopamine receptors were determined using saturating concentrations of dopamine.

| | D2 affinity Ki ± SEM nM | D3 affinity Ki ± SEM nM | D4 affinity Ki ± SEM nM | D2 efficacy $IC_{50}$ ± SEM μM | D3 efficacy $IC_{50}$ ± SEM μM | D4 efficacy $IC_{50}$ ± SEM μM |
|---|---|---|---|---|---|---|
| Buspirone | 484 ± 114 | 98 ± 16 | 29.2 ± 11.3 | 0.67 ± 0.12 | 0.44 ± 0.18 | 0.35 ± 0.06 |
| 5-OH Buspirone | 4010 ± 792 | 261 ± 46 | 107 ± 44.8 | 2.6 ± 1.3 | 0.93 ± 0.46 | 1.4 ± 0.82 |
| 6-OH Buspirone | 5390 ± 425 | 795 ± 84 | 40.4 ± 17.5 | 3.1 ± 1.8 | 4.9 ± 2.8 | 0.85 ± 0.49 |

In summary the available data show that 6-OH-Busp potently binds to serotonin 5-HT1A and dopamine D4 receptors and that 6-OH-Busp is an agonist of 5-HT1A receptors and an antagonist of dopamine receptors.

Pharmacology of 6-OH-Busp—In Vivo

The pharmacokinetics and in vivo potency of 6-OH-Busp in rats has been investigated (Wong et al: Drug Metabolism Disposition 35:1387-1392, 2007). Bioavailability was higher for 6-OH-Busp (19%) compared with that for buspirone (1.4%) and the plasma half-life of 6-OH-Busp slightly longer (1.2±0.2 h) than for buspirone (0.9±0.4 h).

After intravenous infusions to steady-state levels in plasma, 6-OH-buspirone and buspirone increased serotonin 5-HT1A receptor occupancy in a concentration-dependent manner with $EC_{50}$ values of 1.0±0.3 and 0.38±0.06 μM in the dorsal raphe and 4.0±0.6 and 1.5±0.3 μM in the hippocampus, respectively. Both compounds appeared to be ≈4-fold more potent in occupying presynaptic 5-HT1A receptors in the dorsal raphe than the postsynaptic receptors in the hippocampus.

Oral dosing of buspirone in rats resulted in exposures (area under the concentration-time profile) of 6-OH-buspirone and 1-(2-pyrimidinyl)-piperazine (1-PP), another major metabolite of buspirone, that were 12-fold (6-OH-buspirone) and 49-fold (1-PP) higher than the exposure of the parent compound.

In a PET study (Kim et al: International Journal of Neuropsychopharmacology, 2014) using the dopamine D3 preferring ligand, it was found that oral buspirone blocks dopamine D3 receptors at therapeutically relevant doses. Based on the fast metabolism of buspirone to 6-OH-Busp and the effects of this metabolite to human dopamine D3 receptors it was hypothesized that the in vivo receptor blockade of D3 receptors was mediated by 6-HO-Busp. It was furthermore hypothesized that oral buspirone will block dopamine D4 receptors since 6-OH-Busp is a more potent inhibitor of these receptors. Oral buspirone did not cause blockade of D2 receptors.

Method of Treatment

Buspirone metabolites have not previously been used for treatment of movement disorders, neither alone or in combination with other centrally acting drugs.

It is an aspect of the present invention to provide a composition comprising a buspirone metabolite for use in the treatment of a movement disorder.

The composition comprising a buspirone metabolite is in one embodiment used for the treatment, prevention or alleviation of a movement disorder.

In one embodiment the invention is directed to use of a composition comprising a buspirone metabolite for the manufacture of a medicament for the treatment of a movement disorder.

In one embodiment the invention is directed to a method of treating a movement disorder comprising administering a composition comprising a buspirone metabolite to an individual in need thereof.

It is understood that the composition comprising a buspirone metabolite according to the present invention in one embodiment further comprises one or more second active ingredients as outlined herein.

The composition comprising a buspirone metabolite and the movement disorders to be treated are specified herein below.

Composition According to the Invention

A composition according to the present invention is in one embodiment a pharmaceutical composition, a pharmaceutically acceptable composition and/or a pharmaceutically safe composition. A composition according to the present invention comprises at least one active ingredient, which active ingredient in a preferred embodiment is a buspirone metabolite.

In one embodiment a composition according to the present invention comprises one active ingredient. In one embodiment a composition according to the present invention comprises two active ingredients, wherein one is a buspirone metabolite. In one embodiment a composition according to the present invention comprises three active ingredients, wherein one is a buspirone metabolite.

In one embodiment the buspirone metabolite has higher oral bioavailability than parent buspirone.

In one embodiment the buspirone metabolite is selected from the group consisting of 6-OH-Busp, Oxa-Busp, 3-OH-Busp, 5-OH-Busp, 5,6-di-OH-Busp, Busp N-oxide, 5-OH-1-PP and 1-PP, including the racemates and individual enantiomers (S- and R-form) thereof.

In one embodiment there is provided a composition comprising a buspirone metabolite selected from the group consisting of 6-OH-Busp, Oxa-Busp, 3-OH-Busp, 5-OH-Busp, 5,6-di-OH-Busp, Busp N-oxide, 5-OH-1-PP and 1-PP for use in the treatment of a movement disorder.

In one embodiment the buspirone metabolite is 6-OH-Busp, 3-OH-Busp, 5,6-di-OH-Busp or Oxa-Busp, including one or more of the racemate of 6-OH-Busp, 3-OH-Busp, 5,6-di-OH-Busp or Oxa-Busp, the S-form of 6-OH-Busp, 3-OH-Busp, 5,6-di-OH-Busp or Oxa-Busp and/or the R-form of 6-OH-Busp, 3-OH-Busp, 5,6-di-OH-Busp or Oxa-Busp.

In a preferred embodiment the buspirone metabolite is 6-OH-Busp.

In a preferred embodiment the buspirone metabolite is 6-OH-Busp, including one or more of the racemate of 6-OH-Busp, the S-form of 6-OH-Busp and/or the R-form of 6-OH-Busp.

In one embodiment there is provided a composition comprising 6-OH-Busp for use in the treatment of a movement disorder.

Combination Therapy

In one embodiment there is provided a composition comprising a buspirone metabolite and a second active ingredient for use in the treatment of a movement disorder.

Combining the buspirone metabolite and the second active ingredient according to the present invention in one embodiment provides an additive effect compared to use of the buspirone metabolite itself.

Combining the buspirone metabolite and the second active ingredient according to the present invention in one embodiment provides a synergistic effect compared to use of the buspirone metabolite itself.

Combining the buspirone metabolite and the second active ingredient according to the present invention in one embodiment potentiates the therapeutic effect of one or both of each ingredient when compared to use of either ingredient alone.

The buspirone metabolite and the second active ingredient is in one embodiment combined in the same composition, such as a pharmaceutical composition.

The buspirone metabolite and the second active ingredient is in one embodiment contained in separate (or different) compositions, such as separate pharmaceutical compositions.

The buspirone metabolite and the second active ingredient is in one embodiment administered simultaneously, separately or sequentially.

The buspirone metabolite is in one embodiment administered after the second active ingredient. The buspirone metabolite is in another embodiment administered before the second active ingredient. The buspirone metabolite is in another embodiment administered together with the second active ingredient.

Combined 5-HT1 Agonists

The second active ingredient according to the invention is in one embodiment an agonist of two or more of the 5-HT1B, 5-HT1D and 5-HT1F receptors.

In one embodiment there is provided a composition comprising a buspirone metabolite and an agonist of two or more of the 5-HT1B, 5-HT1D and 5-HT1F receptors for use in the treatment of a movement disorder.

The agonist of two or more of the 5-HT1B, 5-HT1D and 5-HT1F receptors is an agonist of two or three serotonin receptors selected from the group consisting of 5-HT1B, 5-HT1D, and 5-HT1F receptors; such as a combined agonist of the 5-HT1B receptor and 5-HT1D receptor, or a combined agonist of the 5-HT1B receptor and 5-HT1F receptor, or a combined agonist of the 5-HT1D receptor and 5-HT1F receptor, or a combined agonist of the 5-HT1B receptor, the 5-HT1D receptor and the 5-HT1F receptor. In one embodiment, said agonist of two or more of the 5-HT1B, 5-HT1D and 5-HT1F receptors is also an agonist of the 5-HT1A receptor (full or partial).

In one embodiment, the agonist of two or more of the 5-HT1B, the 5-HT1D and the 5-HT1F receptors has higher affinity and/or receptor activation efficacy for the 5-HT1D receptor than for the 5-HT1B receptor, or has higher affinity and/or receptor activation efficacy for the 5-HT1D receptor than for the 5-HT1B and 5-HT1F receptors.

In one embodiment the agonist of two or more of the 5-HT1B, 5-HT1D and 5-HT1F receptors is a triptan. A "triptan" in the present context is a compound part of a family of tryptamine-based drugs used as abortive medication in the treatment of migraines and cluster headaches. The triptans are agonists of several of the serotonin receptors, with varying potency for the different 5-HT1 receptor subtypes, primarily 5-HT1B, 5-HT1D, 5-HT1E and/or 5-HT1F receptors.

The agonist of two or more the 5-HT1B, 5-HT1D and 5-HT1F receptors is in one embodiment selected from the group consisting of zolmitriptan ((S)-4-({3-[2-(dimethylamino)ethyl]-1H-indol-5-yl}methyl)-1,3-oxazolidin-2-one), rizatripan (N,N-dimethyl-2-[5-(1H-1,2,4-triazol-1-ylmethyl)-1H-indol-3-yl]ethanamine), sumatriptan (1-[3-(2-dimethylaminoethyl)-1H-indol-5-yl]-N-methyl-methanesulfonamide), naratriptan (N-methyl-2-[3-(1-methylpiperidin-4-yl)-1H-indol-5-yl]ethanesulfonamide), almotriptan (N,N-dimethyl-2-[5-(pyrrolidin-1-ylsulfonylmethyl)-1H-indol-3-yl]-ethanamine), frovatriptan ((+)-(R)-3-methylamino-6-carboxamido-1,2,3,4-tetrahydrocarbazole) and eletriptan ((R)-3-[(-1-methylpyrrolidin-2-yl)methyl]-5-(2-phenylsulfonylethyl)-1H-indole), or pharmaceutically acceptable derivatives thereof.

In one embodiment the triptan is selected from the group consisting of zolmitriptan, rizatriptan, sumatriptan, naratriptan, almotriptan, frovatriptan, avitriptan, alniditan and eletriptan, and pharmaceutically acceptable derivatives thereof.

In one embodiment there is provided a composition comprising a buspirone metabolite and an agonist of two or more of the 5-HT1B, 5-HT1D and 5-HT1F receptors for use in the treatment of a movement disorder, wherein said agonist of two or more of the 5-HT1B, 5-HT1D and 5-HT1F receptors is administered before or before and during administration of the buspirone metabolite.

In one embodiment there is provided a pharmaceutical formulation comprising
a. a matrix constituent comprising an active pharmaceutical ingredient being an agonist of two or more of the 5-HT1B, 5-HT1D and 5-HT1F receptors, said matrix constituent providing for extended release of said active pharmaceutical ingredient, and
b. a constituent comprising an active pharmaceutical ingredient being a buspirone metabolite, said constituent providing for immediate release of said active pharmaceutical ingredient.

In one embodiment said pharmaceutical formulation is a dosage form, such as a solid dosage form, such as a tablet. In one embodiment said dosage form comprises constituents a. and b. in separate compartments or layers; such as an inner core matrix and an outer coating; or a bi-layered tablet. In another embodiment, each of said constituents are provided together in a capsule, wherein said capsule comprises constituents a. and b. as separate granules or pellets. In one embodiment the pharmaceutical formulation comprising a matrix constituent providing for extended release and a constituent providing for immediate release is as described in detail in WO 2013/156035 filed 18 Apr. 2013 (incorporated by reference in its entirety).

Selective Agonist for 5-HT1B, 5-HT1D, 5-5-HT1F

The second active ingredient according to the invention is in one embodiment selected from the group consisting of a selective 5-HT1B receptor agonist, a selective 5-HT1D receptor agonist, a selective 5-HT1E receptor agonist and a selective 5-HT1F receptor agonist. A selective agonist may be a partial or may not be a partial agonist.

In one embodiment there is provided a composition comprising a buspirone metabolite and a second active ingredient selected from the group consisting of a selective 5-HT1B receptor agonist, a selective 5-HT1D receptor agonist, a selective 5-HT1E receptor agonist and a selective 5-HT1F receptor agonist for use in the treatment of a movement disorder.

In one embodiment the selective 5-HT1D receptors agonist is selected from the group consisting of (S)-(−)-1-{2-[4-(4-methoxyphenyl)-1-piperazinyl]ethyl}-N-methyl-isochroman-6-carboxamide (PNU 109291); (S)-(−)-3,4-dihydro-1-[2-[4-(4-aminocarbonyl)-phenyl]-1-piperazinyl]ethyl-N-methyl-1H-2-benzopyran-6-carboxamide (PNU 142633); 3-[4-(3-chlorophenyl)piperazin-1-yl]-1,1-di(phenyl)propan-2-ol (BRL15572); 3-[[(2R)-1-methyl-2-pyrrolidinyl]methyl]-N-(3-nitro-2-pyridinyl)-1H-indol-5-amine (CP 135807); 3-[3-(2-dimethylaminoethyl)-1H-indol-5-yl]-N-(4-methoxybenzyl)acrylamide (GR 46611); and N,N-dimethyl-5-[(5-methyl-1,1-dioxodo-1,2,5-thiadiazolidin-2-yl)methyl]-1H-indole-3-ethanamine succinate (L-703,664 succinate), or a pharmaceutically acceptable derivative thereof.

In one embodiment the selective 5-HT1B receptors agonist is selected from the group consisting of SB 216641 (N-[3-(2-dimethylaminoethoxy)-4-methoxyphenyl]-4-[2-methyl-4-(5-methyl-1,2,4-oxadiazol-3-yl)phenyl]benzamide); CP-94,253 (3-(1,2,5,6-tetrahydro-4-pyridyl)-5-propoxypyrrolo[3,2-b]pyridine); Anpirtoline hydrochloride (6-chloro-2-[piperidinyl-4-thio]pyridine hydrochloride); CGS 12066B dimaleate (7-trifluoromethyl-4-(4-methyl-1-piperazinyl)pyrrolo[1,2-a]-quinoxaline dimaleate); CP 93129 dihydrochloride (1,4-dihydro-3-(1,2,3,6-tetrahydro-4-pyridinyl)-5H-pyrrol[3,2-b]pyridin-5-one dihydrochloride); CP 94253 hydrochloride (5-propoxy-3-(1,2,3,6-tetrahydro-4-pyridinyl)-1H-pyrrolo[3,2-b]pyridine hydrochloride); GR 46611 (3-[3-(2-dimethylaminoethyl)-H-indol-5-yl]-N-(4-methoxybenzyl) acrylamide); L 694247 (2-{5-[3-(4-methylsulfonylamino)benzyl-1,2,4-oxadiazol-5-yl]-1H-indole-3-yl}ethylamine); and SKF 99101H (1'-methyl-5-{[2'-methyl-4'-(5-methyl-1,2,4-oxadiazol-3-yl)biphenyl-4-yl]carbonyl}-2,3,6,7-tetrahydrospiroifuro[2,3-f]indole-3,4'-piperidine), or a pharmaceutically acceptable derivative thereof.

In one embodiment the selective 5-HT1F receptors agonist is selected from the group consisting of COL-144 (lasmiditan), LY573144 (2,4,6-trifluoro-N-[6-[(1-methylpiperidin-4-yl)carbonyl]pyridin-2yl]benzamide)), LY334370 (4-fluoro-N-[3-(1-methylpiperidin-4-yl)-1H-indol-5-yl]benzamide) and LY344864 (N-(6-dimethylamino-6,7,8,9-tetrahydro-5H-carbazol-3-yl)-4-fluorobenzamide), or a pharmaceutically acceptable derivative thereof.

In one embodiment there is provided a composition comprising a buspirone metabolite and a second active ingredient being an agonist of two or more the 5-HT1B, 5-HT1D and 5-HT1F receptors and a third active ingredient for use in the treatment of a movement disorder.

A Modulator of Glutamate Neurotransmission

The second active ingredient according to the invention is in one embodiment a modulator of glutamate neurotransmission.

In one embodiment there is provided a composition comprising a buspirone metabolite and a modulator of glutamate neurotransmission for use in the treatment of a movement disorder.

Glutamate is a major mediator of excitatory signals in the mammalian central nervous system and is involved in most aspects of normal brain function including cognition, memory and learning. Glutamate exerts its signalling function by binding to and activating cell surface glutamate receptors. Several subtypes of glutamate receptors have been identified: NMDA receptor (N-methyl-D-aspartate receptor; NMDAR), AMPA receptor (α-amino-3-hydroxy-5-methyl-4-isoxazolepropionic acid receptor, quisqualate receptor, AMPAR), metabotropic glutamate receptors (mGluR) and kainite receptors. NMDAR, AMPAR and kainate receptors are ionotropic receptors (ligand-gated ion channels), while metabotropic glutamate receptors are not.

Glutamate concentration in the extracellular fluid of the brain is regulated by cellular uptake of glutamate. Glutamate uptake is mediated by a family of special transporter proteins which act as pumps. Glutamate is taken up into both glial cells and nerve terminals. The former is believed to be the more important from a quantitative point of view. Glutamate taken up by astroglial cells is converted to glutamine which is inactive since it cannot activate glutamate receptors, and is released from the glial cells into to extracellular fluid. Nerve terminals take up glutamine and convert glutamine back to glutamate. This process allows glutamate to be inactivated by glial cells and transported back to neurons in an inactive form.

Glutamate neurotransmission may be modulated according to the present invention in any way known to the skilled person. In one embodiment a modulator of glutamate neurotransmission is a glutamate receptor modulator.

In one embodiment a modulator of glutamate neurotransmission is a glutamate receptor antagonist, such as a postsynaptic glutamate receptor antagonist.

In one embodiment a modulator of glutamate neurotransmission is a glutamate receptor agonist, such as a presynaptic glutamate receptor agonist.

In another embodiment a modulator of glutamate neurotransmission is an agent that directly or indirectly affects extracellular glutamate concentration.

In one embodiment a modulator of glutamate neurotransmission is an agent that inhibits glutamate release.

In one embodiment a modulator of glutamate neurotransmission is an agent that increases glutamate uptake (e.g. stimulates glutamate transporters).

a) Glutamate Receptor Modulator

In one embodiment there is provided a composition comprising a buspirone metabolite and a glutamate receptor modulator for use in the treatment of a movement disorder.

In one embodiment said glutamate receptor modulator inhibits the effects of native glutamate on its postsynaptic receptors and/or inhibits presynaptic release of glutamate.

In one embodiment said glutamate receptor modulator include glutamate receptor antagonists and negative allosteric modulators (NAM). In another embodiment said glutamate receptor modulator include glutamate receptor agonists and positive allosteric modulators (PAM).

In one embodiment there is provided a composition comprising a buspirone metabolite and a glutamate receptor modulator selected from the group consisting of NMDA receptor antagonists, AMPA receptor antagonists, kainite receptor antagonists, AMPAR/kainite receptor antagonists, Group 1 mGluR antagonists and Group 2/3 mGluR agonists.

In one embodiment there is provided a composition comprising a buspirone metabolite and a glutamate receptor antagonist and/or negative allosteric modulator for use in the treatment of a movement disorder.

The NMDA receptor forms a heterotetramer between two GluN1 and two GluN2 subunits (the subunits were previously denoted as NR1 and NR2). There are eight variants of the NR1 subunit and four distinct isoforms of the NR2 subunit. In one embodiment an NMDAR antagonist binds to one or more of the NMDA subunits, specifically or preferentially.

The NMDA receptor antagonist is in one embodiment a non-selective or broad spectrum antagonist, or a NR2A subunit preferring or selective antagonist, or a NR2B subunit preferring or selective antagonist.

In one embodiment the NMDA receptor antagonist is selected from the group consisting of amantadine, memantine, MK-801 (dizocilpine), CPP (midafotel), phencyclidine (PCP), remacemide, LY-235,959, ifenprodil, traxoprodil (CP-101,606), besonprodil, ro-256981, Ro-631908, ketamine, S-(+)-ketamine, methoxetamine (3-MeO-2-Oxo-PCE), dextromethorphan, dextrorphan, AP5 (APV; (2R)-amino-5-phosphonovaleric acid); riluzole, dexanabinol (HU-211); conantokins (Con-G, Con-T, Con-R, Con-L, Con-Pr1, Con-Pr2, Con-Pr3, Con-P, Con-E, Con-R1-A, Con-Br) huperzine A, atomoxetine, ketobemidone, methadone, dextropropoxyphene, tramadol, kratom alkaloids and ibogaine, or derivatives thereof.

AMPARs are composed of four types of subunits, designated as GluR1, GluR2, GluR3 and GluR4, which combine to form tetramers. Each subunit of the AMPAR has a binding site for glutamate. In one embodiment an AMPAR antagonist binds to one or more of the AMPAR subunits, specifically or preferentially.

In one embodiment the AMPA receptor antagonist is selected from the group consisting of tezampanel (LY-293,558; (3S,4aR,6R,8aR)-6-[2-(1H-tetrazol-5-yl)ethyl]decahydroisoquinoline-3-carboxylic acid); talampanel (GYKI 537773; LY300164; (8R)-7-Acetyl-5-(4-aminophenyl)-8,9-dihydro-8-methyl-7H-1,3-dioxolo[4,5-h][2,3]benzodiazepine); perampanel (5'-(2-cyanophenyl)-1'-phenyl-2,3'-bipyridinyl-6'(1'H)-one); GYKI-53,655; GYKI-52,466; NBQX (2,3-dihydroxy-6-nitro-7-sulfamoyl-benzo[f]quinoxaline-2,3-dione); CNQX (6-cyano-7-nitroquinoxaline-2,3-dione); DNQX (6,7-dinitroquinoxaline-2,3-dione); topiramate, ethanol, L-theanine and kynurenic acid, or derivatives thereof.

There are five types of kainate receptor subunits, $GluR_5$, $GluR_6$, $GluR_7$, KA1 and KA2, which are similar to AMPA and NMDA receptor subunits and can be arranged in different ways to form a tetramer. In one embodiment a kainate receptor antagonist binds to one or more of the kainate receptor subunits, specifically or preferentially.

In one embodiment the kainate receptor antagonist is selected from the group consisting of CNQX (6-cyano-7-nitroquinoxaline-2,3-dione); DNQX (6,7-dinitroquinoxaline-2,3-dione); tezampanel (LY-293,558; (3S,4aR,6R,8aR)-6-[2-(1H-tetrazol-5-yl)ethyl]decahydroisoquinoline-3-carboxylic acid); NS102 (5-Nitro-6,7,8,9-tetrahydro-1H-benzo[g]indole-2,3-dione 3-oxime); topiramate, ethanol and kynurenic acid, or derivatives thereof.

Some compounds are AMPAR/kainite receptor antagonists, i.e. they target both types of receptors (e.g. topiramate).

mGluR's are 7TM G-protein coupled receptors which can be divided into Group 1 mGluR (mGluR1, mGluR5), Group 2 mGluR (mGluR2, mGluR3) and Group 3 mGluR (mGluR4, mGluR6, mGluR7, mGluR8). The mGluRs are characterized based on their structure, distribution and physiology.

While Group 1 mGluR's are postsynaptic, the Group 2 and Group 3 mGluR's are presynaptic primarily regulating release of glutamate or other neurotransmitters.

A glutamate receptor modulator according to the present invention in one embodiment modulates a mGluR.

A glutamate receptor modulator according to the present invention is in one embodiment a postsynaptic mGluR antagonist.

A glutamate receptor modulator according to the present invention is in one embodiment a presynaptic mGluR agonist.

A glutamate receptor modulator according to the present invention in one embodiment inhibits Group 1 mGluRs (receptor antagonist or a NAM).

A glutamate receptor modulator according to the present invention in one embodiment regulates/inhibits release of glutamate from Group 2 and/or Group 3 mGluRs (receptor agonist or PAM).

In one embodiment the glutamate receptor modulator according to the present invention is a mGluR antagonist, such as a Group 1 mGluR antagonist. In one embodiment the Group 1 mGluR antagonist is an mGluR1 antagonist or an mGluR5 antagonist.

In one embodiment the glutamate receptor modulator according to the present invention is a mGluR agonist, such as a Group 2/3 mGluR agonist. In one embodiment the Group 2/3 mGluR agonist is selected from the group consisting of a mGluR2 agonist, a mGluR3 agonist, a mGluR4 agonist, a mGluR6 agonist, a mGluR7 agonist and a mGluR8 agonist (or PAM).

In one embodiment the Group 1 mGluR antagonist (mGluR5 antagonist) is selected from the group consisting of mavoglurant (AFQ056), dipraglurant, 2-methyl-6-(phenylethynyl)pyridine (MPEP); 3-((2-methyl-4-thiazolyl)ethynyl)pyridine (MTEP); fenobam (1-(3-chlorophenyl)-3-(3-methyl-5-oxo-4H-imidazol-2-yl)urea); and derivatives thereof.

In one embodiment the Group 2 mGluR agonist (mGluR2/3 agonist) is selected from the group consisting of LY 379268, DCG-IV, APICA (1-amino-5-phosphonoindan-1-carboxylic acid) and EGLU ((2S)-α-ethylglutamic acid), and derivatives thereof.

In one embodiment the Group 3 mGluR agonist (mGluR4 agonist) is selected from the group consisting of eglumegad (LY354740); LY544344; LSP-13081; LSP-12111; LuAF-21934; VU-400195 and VU-0354770, and derivatives thereof.

b) Inhibitors of Glutamate Release

In one embodiment there is provided a composition comprising a buspirone metabolite and an inhibitor of glutamate release from cortico-striatal receptors for use in the treatment of a movement disorder.

In one embodiment the agent that inhibits glutamate release is riluzole. In one embodiment the agent that inhibits glutamate release is an antiepileptic agent. In one embodiment the agent that inhibits glutamate release is topiramate.

Ion Channel Inhibitor

Modulators of certain neuronal ion channels are known to affect neurotransmitter release or neurotransmitter receptor activity. Antagonists of ion channels that reduce or inhibit ion fluxes trough biological membranes and thereby changes membrane potential can affect neurotransmitter release, uptake or receptor activity.

The second active ingredient according to the invention is in one embodiment an ion-channel inhibitor or ion-channel blocker or ion-channel antagonist. These terms are used interchangeably herein.

In one embodiment there is provided a composition comprising a buspirone metabolite and an ion-channel inhibitor for use in the treatment of a movement disorder.

In one embodiment the ion-channel inhibitor is a calcium channel antagonist, a potassium channel antagonist, or a sodium channel antagonist, or a combined potassium channel and sodium channel antagonist.

In one embodiment the ion-channel inhibitor binds to a neuronal ion channel selected from the group consisting of T-Type calcium channels, L-Type calcium channels, $K^+$ channels and $Na^+$ channels.

In one embodiment the ion-channel antagonist is selected from the group consisting of a T-Type calcium channel antagonist, an L-Type calcium channels antagonist, a $K^+$ channel antagonist and/or a $Na^+$ channel antagonist. It follows that the ion-channel antagonist may have effect on one specific ion-channel or it may have effect on more than one such as at least two different ion channels.

In one embodiment the ion-channel antagonist is zonizamide. In one embodiment the ion-channel antagonist is topiramate.

Calcium channel antagonists are a number of medications that disrupts the movement of calcium ($Ca^{2+}$) through calcium channels. Calcium channel blockers are mainly used as antihypertensive drugs.

In one embodiment the ion-channel inhibitor is a T-type calcium channel selected from the group consisting of zonizamide, ethozuximide, mibefradil, flunarizine, trimethadione, Z944 and Z123212.

In one embodiment the calcium channel antagonist is a dihydropyridine calcium channel blocker, in one embodiment selected from the group consisting of: Nimodipine (Nimotop), Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Isradipine (DynaCirc, Prescal), Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas).

In one embodiment the calcium channel antagonist is a non-dihydropyridine calcium channel blocker, in one embodiment selected from the group consisting of: Phenylalkylamine calcium channel blockers including Verapamil (Calan, Isoptin), Gallopamil and Fendiline; Benzothiazepine calcium channel blockers including Diltiazem (Cardizem); Ziconotide; and nonselective calcium channel antagonists such as mibefradil, bepridil, flunarizine, fluspirilene and fendiline.

Potassium channel blockers are agents which interfere with conduction through potassium channels.

In one embodiment the potassium channel antagonist is selected from the group consisting of Amiodarone, Dofetilide, Sotalol, Ibutilide, Azimilide, Bretylium, Clofilium, E-4031, Nifekalant, Tedisamil, Sematilide, Dalfampridine and Sulfonylureas.

In one embodiment the sodium channel antagonist is selected from the group consisting of remacemide, zonizamide and topimirate.

In one embodiment the ion-channel antagonist is selected from the group consisting of kavalactones such as kavain.

In one embodiment there is provided a composition comprising a buspirone metabolite and a KCNQ channel modulator.

The KCNQ channels also designated Kv7, is a voltage-dependent potassium channel family of which the genes encoding for subunits Kv7.1-Kv7.5 have currently been characterised. Mutations in four out of five Kv7 genes have been shown to underlie diseases including cardiac arrhythmias, deafness and epilepsy. All KCNQ channels share a typical topological design, consisting of a functional channel formed by four subunits; each comprising six transmembrane segments termed S1 to S6. KCQN channels can be homomers formed by the same type of subunit, or heteromers comprising different types of subunits.

A KCNQ activator is capable of binding to a KCNQ channel and triggering one or more effects, such as stabilizing the open conformation of the channel and facilitating series of conformational changes to open the channel, increased channel open times, and decreased longest closed times. As a result of these effects, the transportation of ions through the channel is increased. A number of KCNQ activating compounds have been described in the art (for example Wulff al. Nat Rev Drug Discov. 2009; 8(12):982-1001 and Xiong et al. Trends Pharmacol Sci. 2008; 29(2): 99-107).

In a more preferred embodiment, the KCNQ activator activates one or more KCNQ channels selected from homomeric KCNQ channels selected from the group of KCNQ channels comprising Kv7.2, Kv7.3, Kv7.4, Kv7.5 subunits or a heteromeric KCNQ channels the selected from the group of KCNQ channels comprising Kv7.2 and Kv7.3 subunits (Kv7.2/3 channels), or comprising Kv7.3 and Kv7.4 subunits (Kv7.3/4 channels), or comprising Kv7.3 and Kv7.5 subunits (Kv7.3/5 channels).

In another embodiment of the present invention, the KCNQ channel activator is selected from the group consisting of retigabine (N-(2-amino-4-(4-fluorobenzylamino)-phenyl carbamic acid) ethyl ester); flupirtine (ethyl-(2-amino-6-[(4-fluorobenzyl)amino]pyridin-3-yl) carbamate): ICA-27243 (N-(6-chloro-pyridin-3-yl)-3,4-difluoro-benzamide); Maxipost (the racemic mixture of BMS-204352 ((R/S)-(5-chloro-2-methoxyphenyl)-3-fluro-6-(trifluoromethyl)-2,3-dihydro-1H-indol-2-one [(R)-3-(5-chloro-2-methoxyphenyl)-3-fluoro-6-(trifluoromethyl)-1,3-dihydro-2H-indole-2-one])); the S enantiomer of BMS-204352 (S)-(5-chloro-2-methoxyphenyl)-3-fluro-6-(trifluoromethyl)-2,3-dihydro-1H-indol-2-one [(R)-3-(5-chloro-2-methoxyphenyl)-3-fluoro-6-(trifluoromethyl)-1,3-dihydro-2H-indole-2-one]); substituted pyridines such as those described in WO 2006092143 and WO 2011026890 (both of which are incorporated by reference herein); acrylamide (S)-1 ((S)—N-[1-(3-morpholin-4-yl-phenyl)-ethyl]-3-phenyl-acrylamide); acrylamide (S)-2; N-phenylanthralinic acid derivatives such as diclofenac, flufenamic acid, meclofenamic acid, NH6, and niflumic acid; L-364373; zinc pyrithione (bis(1-hydroxy-2(1H)-pyridineselonato-O,S) zinc); and ICA-105665; or pharmaceutically acceptable derivatives thereof.

Movement Disorders According to the Invention

The present invention relates to a composition comprising a buspirone metabolite for use in the treatment of movement disorders. The term treatment according to the present invention includes treatment, prevention/prophylaxis (reduction of risk) and amelioration.

In one embodiment the movement disorder is a disorder associated with altered or impaired synaptic dopamine levels.

In one embodiment, the movement disorder according to the present invention is selected from the group consisting of Parkinson's disease, movement disorders associated with Parkinson's disease, bradykinesia, akinesia, dyskinesia, L-DOPA induced dyskinesia, tardive dyskinesia, ataxia, akathisia, dystonia, essential tremor, Huntington's disease, myoclonus, Rett syndrome, Tourette syndrome, Wilson's disease, chorea, Machado-Joseph disease, restless leg syndrome, spasmodic torticollis, geniospasm, or movement disorders associated therewith.

Movement disorders according to the present invention may also be associated with use of neuroleptic drugs, idiopathic disease, genetic dysfunctions, infections or other conditions which lead to dysfunction of the basal ganglia and/or lead to altered synaptic dopamine levels.

Parkinson's disease is associated with muscle rigidity, tremor, postural abnormalities, gait abnormalities, a slowing of physical movement (bradykinesia), and in extreme cases a loss of physical movement (akinesia). PD is caused by degeneration and death of dopaminergic neurons in substantia nigra pars compacta, and leads to dysfunctional regulation of dopamine neurotransmission.

In one particular embodiment of the present invention the movement disorder is Parkinson's disease. In one particular embodiment of the present invention the movement disorder is Parkinson's disease or the associated movement disorders akinesia, dyskinesia and bradykinesia, or movement disorders associated with Parkinson's disease such as L-DOPA induced dyskinesia. In one preferred embodiment of the present invention, the movement disorder is tardive dyskinesia.

In another embodiment of the present invention, the movement disorder is caused by or associated with medication of antipsychotics such as haloperidol, droperidol, pimozide, trifluoperazine, amisulpride, risperidone, aripiprazole, asenapine, and zuclopenthixol, antidepressants such as fluoxetine, paroxetine, venlafaxine, and trazodone, antiemetic drugs such as dopamine blockers for example metoclopramide (reglan) and prochlorperazine (compazine).

In yet another embodiment of the present invention, the movement disorder is caused by or associated with withdrawal of opioids, barbiturates, cocaine, benzodiazepines, alcohol, or amphetamines.

It is an aspect of the present invention to provide a composition as defined herein for use in a method for the treatment of a movement disorder.

It is an aspect of the present invention to provide a composition as defined herein for manufacture of a medicament for the treatment of a movement disorder.

In one embodiment, the composition as defined herein for use in a method for the treatment of a movement disorder is administered to an individual in need thereof.

An individual in need as referred to herein, is an individual that may benefit from the administration of a compound or pharmaceutical composition according to the present invention. Such an individual may suffer from a movement disorder or be in risk of suffering from a movement disorder. The individual may be any human being, male or female, infant, middle-aged or old. The movement disorder to be treated or prevented in the individual may relate to the age of the individual, the general health of the individual, the medications used for treating the individual and whether or not the individual has a prior history of suffering from diseases or disorders that may have or have induced movement disorders in the individual.

The present invention relates to a composition comprising a buspirone metabolite for use in the prevention of movement disorders, wherein said composition is administered to an individual having a risk (e.g. an increased risk) of suffering from a movement disorder. In one embodiment said individual having a risk of suffering from a movement disorder is a person which is, or is to be, treated with a dopamine prodrug such as L-DOPA (e.g. levodopa).

Further Active Ingredients

The compounds or pharmaceutical compositions of the present invention may be combined with or comprise one or more further active ingredients which are understood as other therapeutic compounds (active pharmaceutical ingredients) or pharmaceutically acceptable derivatives thereof.

The further active ingredient(s) is in one embodiment administered in addition to the buspirone metabolite. The further active ingredient(s) is in another embodiment administered in addition to the buspirone metabolite and the second active ingredient.

A further active ingredient according to the present invention is in one embodiment one or more agents selected from the group consisting of agents increasing the dopamine concentration in the synaptic cleft, dopamine, a dopamine prodrug, L-DOPA (e.g. levodopa), dopamine receptor agonists including but not limited to bromocriptine, pergolide, pramipexole, ropinirole, piribedil, cabergoline, apomorphine, lisuride, and pharmaceutically acceptable derivatives thereof.

Further active ingredients is in one embodiment selected from compounds which ameliorate PD symptoms or which are used for treatment of PD, including but not limited to peripheral inhibitors of the transformation of L-DOPA (or other dopamine prodrugs) to dopamine, for example DOPA decarboxylase inhibitors such as carbidopa (lodosyn) or benserazide, catechol-O-methyl transferase (COMT) inhibitors such as for example tolcapone, entacapone and nitecapone, MAO-B inhibitors such as for example selegiline and rasagiline, serotonin receptor modulators, kappa opioid receptors agonists such as for example TRK-820 ((E)-N-[17-cyclopropylmethyl)-4,5α-epoxy-3,14-dihydroxymorphinan-6β-yl]-3-(furan-3-yl)-N-methylprop-2-enamide monohydrochloride).

In a preferred embodiment of the present invention, a further active ingredient is a dopamine prodrug, such as L-DOPA or a pharmaceutically acceptable derivative thereof. Thus in one preferred embodiment, a dopamine prodrug, such as L-DOPA (e.g. levodopa) is used in combination with a composition comprising a buspirone metabolite according to the present invention.

In one embodiment of the present invention, the compound or pharmaceutical composition is combined with two or more further active ingredients. Such two further active ingredients is in one embodiment a dopamine prodrug such as L-DOPA in combination with a decarboxylase inhibitor. Thus in an embodiment of the present invention, the two or more further active ingredients comprise a dopamine prodrug such as L-DOPA and carbidopa, or L-DOPA and benserazide.

In another embodiment, such two further active ingredients are a dopamine prodrug such as L-DOPA in combination with a COMT inhibitor, wherein the COMT inhibitor in one embodiment is tolcapone, entacapone or nitecapone.

The further active ingredients according to the present invention can also be included in the same formulations such as for example the L-DOPA/benserazide and carbidopa/levodopa (sometimes referred to as levocarb) formulations sinemet, parcopa, madopar, kinson, atamet, or L-DOPA/COMT inhibitor formulations such as for example stalevo (carbidopa/levodopa and entecapone).

In one embodiment, the composition according to the present invention is to be administered in combination with a separate L-DOPA or L-DOPA/benzerazide preparation, separately, simultaneously or sequentially. In a particular embodiment, said composition is administered before or simultaneously with treatment of the separate L-DOPA or L-DOPA/benzerazide preparation.

In one embodiment the present invention relates to a composition comprising a buspirone metabolite as defined herein for increasing the effect of a dopamine prodrug such as L-DOPA or levodopa in an individual, and/or to reduce the decreased effect over time of a dopamine prodrug such as L-DOPA or levodopa in an individual, wherein said individual in one embodiment has, or is at risk of having, a movement disorder.

Dosage

According to the present invention, buspirone metabolites are administered to an individual in need of treatment in pharmaceutically effective doses or therapeutically effective amounts. A therapeutically effective amount of a compound according to the present invention is an amount sufficient to cure, prevent, reduce the risk of, alleviate or partially arrest the clinical manifestations of a given disease or movement disorder and its complications. The amount that is effective for a particular therapeutic purpose will depend on the severity and the sort of the movement disorder as well as on the weight and general state of the subject. The compounds or compositions of the present invention may be administered one or several times per day, such as from 1 to 2 times per day, such as from 2 to 3 times per day, such as from 3 to 4 times per day, such as from 4 to 5 times per day, such as from 5 to 6 times per day, wherein administration from 1 to 3 times per day is preferred. In another embodiment the compound or composition of the invention may be administered less than once a day, for instance one every second day, once every third day, one every fourth day, once every fifth day, one every sixth day, once every seventh day, or once every 2 weeks.

The administration of compounds, pharmaceutical compositions and second or further active ingredients according to the present invention may be administered to an individual at various time points of treatment. The treatment may be done over one continued period, or in intervals with periods in between wherein the administration of one or more compounds, pharmaceutical compositions and further active ingredients according to the present invention is stopped, decreased or altered. Such treatment periods or non-treatment periods may vary in length, and can be from 1 day to 42 days, such as 1 to 2 days, 2 to 3 days, 3 to 4 days, 4 to 5 days, 5 to 6 days, 6 to 7 days, 7 to 14 days, 14 to 21 days, 21 to 28 days, 28 to 35 days or 35 to 42 days.

In one embodiment the buspirone metabolite, and/or the second active ingredient, is administered in doses of 0.5 mg/day to 1000 mg/day, such as 0.5 mg/day to 1 mg/day, such as 1 to 2 mg/day, such as 2 to 3 mg/day, such as 3 to 4 mg/day, such as 4 to 5 mg/day, such as 5 to 6 mg/day, such as 6 to 7 mg/day, such as 7 to 8 mg/day, such as 8 to 9 mg/day, such as 9 to 10 mg/day, such as 10 to 15 mg/day, such as 15 to 20 mg/day, such as 20 to 25 mg/day, such as 25 to 30 mg/day, such as 30 to 40 mg/day, such as 40 to 50 mg/day, such as 50 to 75 mg/day, such as 75 to 100 mg/day, such as 100 to 150 mg/day, such as 150 to 200 mg/day, such as 200 to 250 mg/day, such as 250 to 300 mg/day, such as 300 to 400 mg/day, such as 400 to 500 mg/day, such as 500 to 600 mg/day, such as 600 to 700 mg/day, such as 700 to 800 mg/day, such as 800 to 900 mg/day, such as 900 to 1000 mg/day.

In one embodiment of the present invention, a single dose of the buspirone metabolite, and/or the second active ingredient, is administered and may comprise 0.05 mg/kg bodyweight to 100 mg/kg bodyweight, such as 0.05 to 0.1 mg/kg bodyweight, such as 0.1 to 0.2 mg/kg bodyweight, such as 0.2 to 0.5 mg/kg bodyweight, such as 0.5 to 1 mg/kg bodyweight, such as 1 to 2 mg/kg bodyweight, such as 2 to 3 mg/kg bodyweight, such as 3 to 4 mg/kg bodyweight, such as 4 to 5 mg/kg bodyweight, such as 5 to 10 mg/kg bodyweight, such as 10 to 15 mg/kg bodyweight, such as 15 to 20 mg/kg bodyweight, such as 20 to 30 mg/kg bodyweight, such as 30 to 40 mg/kg bodyweight, such as 40 to 50 mg/kg bodyweight, such as 50 to 75 mg/kg bodyweight, such as 75 to 100 mg/kg bodyweight.

In one embodiment the composition of the present invention is administered as long as a movement disorder or an increased risk of developing a movement disorder is present.

Administration Route

It will be appreciated that the preferred route of administration will depend on the general condition and age of the subject to be treated, the nature of the condition to be treated, the location of the tissue to be treated in the body and the active ingredient(s).

In one embodiment of the present invention, the route of administration allows for the agent to cross the blood-brain barrier.

Systemic Treatment

Systemic treatment according to the present invention is capable of introducing the compound or composition into the blood stream to ultimately target the sites of desired action.

Systemic treatment includes administration via the enteral route and the parenteral route including oral, rectal, nasal, vaginal, rectal, pulmonary, bronchial, buccal, sublingual, transdermal, topical, intracisternal, intraperitoneal, subcutaneous, intramuscular, intrathecal, intravenous and intradermal administration. Appropriate dosage forms for such administration may be prepared by conventional techniques.

Local Treatment

The agent according to the invention may be used as a local treatment, i.e. be introduced directly to the site(s) of action. Accordingly, the agent may be applied to the skin or mucosa directly, or the agent may be injected into the site of action, for example into the diseased tissue or to an end artery leading directly to the diseased tissue (intracavernous, intravitreal, intra-articular, intracerebral, intrathecal, epidural).

EXAMPLES

Example I

The 6-OHDA rat model as described below is useful for evaluation of buspirone metabolites for treatment of movement disorders associated with Parkinson's disease and LID.

The 6-OHDA Rat Model

6-OHDA (6-hydroxydopamine) is a neurotoxin that selectively kills dopaminergic and noradrenergic neurons and induces a reduction of dopamine levels in the brain. Administration of L-DOPA to unilaterally 6-OHDA-lesioned rats induces abnormal involuntary movements (AIMs). These are axial, limb and oral movements that occur only on the body side that is ipsilateral to the lesion. AIM rat models have been shown useful because they respond to a number of drugs which have been shown to suppress dyskinesia (including PD) in humans.

Test Procedure:

Animals: 90 experimentally-naïve, male, Sprague-Dawley rats at body weight of 200 to 250 g arrive at the laboratory at least 1 week prior to behavioural testing. Rats are housed in groups of n=2/cage. Animals have ad libitum access to standard rodent chow and water. Animal housing and testing rooms are maintained under controlled environmental conditions and are within close proximity of each other. Animal housing rooms are on a 12-hour light-dark cycle with lights on at 6:00 AM and maintained at 70° F./21° C. (range: 68-72° F./20-22° C.) with a humidity range of 20-40%. Testing rooms are maintained at 68-72° F. with a humidity range of 20-40%.

DA (dopamine)-denervating lesions are performed by unilateral injection of 6-OHDA in the ascending nigrostriatal pathway. Rats are anesthetized with pentobarbital sodium 40 mg/kg (i.p.) and positioned in a stereotactic frame. 6-OHDA is injected into the right ascending DA bundle at the following coordinates (in mm) relative to bregma and dural surface: (1) toothbar position −2.3, A=−4.4, L=1.2, V=7.8, (7.5 ug 6-OHDA), (2) toothbar position +3.4, A=−4.0, L=0.8, V=8.0 mm (6 ug 6-OHDA). The neurotoxin injections are performed at a rate of 1 ul/min, and the injection cannula is left in place for an additional 2-3 min thereafter. Two weeks after surgery rats with nearly complete (>90%) lesions are selected by means of an amphetamine-induced rotation test. The animals are placed in plastic Perspex bowls (30 cm in diameter) and the rotational behavior (360° turns) is recorded by an automated rotometer for 90 min after the i.p. injection of 2.5 mg/kg d-amphetamine sulphate. Animals that are exhibiting 56 full body turns/min towards the side of the DA deficiency are included in the study. Animals are then allocated into two well-matched sub-groups (according to the amphetamine rotation) and receive daily treatment.

Drugs and Treatment Regimens

Drug Treatment:

L-DOPA methyl ester (Sigma-Aldrich, Germany) is given at the dose of 6 mg/kg, combined with 15 mg/kg of benserazide HCl (Sigma-Aldrich, Germany). Chronic treatment with this dose of L-DOPA and benserazide is given for 3 weeks to all the rats with good lesions in order to induce a gradual development of dyskinetic-like movements. Thereafter, rats that have not developed dyskinesia are excluded from the study, and the rats with a cumulative AIM score ≥28 points over five testing sessions (dyskinesia severity ≥grade 2 on each axial, limb and orolingual scores) are kept on a drug treatment regimen of at least two injections of L-DOPA/benserazide per week in order to maintain stable AIM scores. The selected rats are allocated groups of 9-12 animals each, which are balanced with the respect to AIM severity. The animals are then treated with the drug and drug combinations as described below.

Prevention:

In the prevention study rats are treated with L-DOPA methyl ester (6 mg/kg i.p. plus benserazide 15 mg/kg) in combination with buspirone or 6-OH buspirone (0.5-10 mg/kg), and possibly also a combination agent for 3 weeks (such as zolmitriptan (0.5 mg/kg-20 mg/kg i.p.). At the end of this treatment (treatment period 1), animals receive a low dose of apomorphine (0.02 mg/kg, s.c.) and are tested for apomorphine-induced AIMs in order to investigate the sensitization state of the DA receptors. Treatments are then continued so that animals are treated only with L-DOPA for an additional two weeks (treatment period 2). Animals are injected daily and tested every second day for L-DOPA-induced dyskinesia throughout the experimental periods 1 and 2 and then sacrificed for HPLC analysis of DA, serotonin and metabolites.

To determine the effects of specific doses of buspirone metabolites the following group setting can be used:

Vehicle: (saline, i.p. or s.c., 30 min before L-DOPA, n=6)
Buspirone (0.5 mg/kg, i.p. or s.c., n=6)
6-OH Buspirone (1 mg/kg i.p. or s.c.)
6-OH Buspirone (5 mg/kg i.p. or s.c.)

Buspirone and 6-OH Buspirone is given 30 minutes before L-DOPA.

L-DOPA Induced AIMs and Drugs Screening Test

AIMs ratings are performed by an investigator who is kept unaware of the pharmacological treatment administered to each rat (experimentally blinded). In order to quantify the severity of the AIMs, rats are observed individually in their standard cages every 20th minute at 20-180 min after an injection of l-DOPA. The AIM's are classified into four subtypes:

(A) axial AIMs, i.e., dystonic or choreiform torsion of the trunk and neck towards the side contralateral to the lesion. In the mild cases: lateral flexion of the neck or torsional movements of the upper trunk towards the side contralateral to the lesion. With repeated injection of L-DOPA, this movement may develop into a pronounced and continuous dystonia-like axial torsion.

(B) limb AIMs, i.e., jerky and/or dystonic movements of the forelimb contralateral to the lesion. In mild cases: hyperkinetic, jerky stepping movements of the forelimb contralateral to the lesion, or small circular movements of the forelimb to and from the snout. As the severity of dyskinesia increases (which usually occurs with repeated administration of L-DOPA), the abnormal movements increase in amplitude, and assume mixed dystonic and hyperkinetic features. Dystonic movements are caused by sustained co-contraction of agonist/antagonist muscles; they are slow and force a body segment into unnatural positions. Hyperkinetic movements are fast and irregular in speed and direction. Sometimes the forelimb does not show jerky movements but becomes engaged in a continuous dystonic posture, which is also scored according to the time during which it is expressed.

(C) orolingual AIMs, i.e., twitching of orofacial muscles, and bursts of empty masticatory movements with protrusion of the tongue towards the side contralateral to the lesion. This form of dyskinesia affects facial, tongue, and masticatory muscles. It is recognizable as bursts of empty masticatory movements, accompanied to a variable degree by jaw opening, lateral translocations of the jaw, twitching of facial muscles, and protrusion of the tongue towards the side contralateral to the lesion. At its extreme severity, this subtype of dyskinesia engages all the above muscle groups with notable strength, and may also become complicated by self-mutilative biting on the skin of the forelimb contralateral to the lesion (easily recognizable by the fact that a round spot of skin becomes devoid of fur.

(D) locomotive AIMs, i.e., increased locomotion with contralateral side bias. The latter AIM subtype was recorded in conformity with the original description of the rat AIM scale, although it was later established that locomotive AIMs do not provide a specific measure of dyskinesia, but rather provide a correlate of contralateral turning behaviour in rodents with unilateral 6-OHDA lesions.

Each of the four subtypes are scored on a severity scale from 0 to 4, where 0=absent, 1=present during less than half of the observation time, 2=present for more than half of the observation time, 3=present all the time but suppressible by external stimuli, and 4=present all the time and not suppressible by external stimuli. Axial, limb and orolingual AIMs are found to be modulated in a similar way by all the tested substances.

Rats are tested for AIMs using the sum of locomotive (LO) oraxial (AX), limb (LI), and orolingual (OL) AIM scores per testing session for statistical analyses. The results show the compounds that significantly reduce L-DOPA-induced dyskinesia.

Example II

The present study describes the evaluation of buspirone and 6-OH Busp; a combination of 6-OH-Busp and fenobam in the 6-OHDA rat model, and a combination of 6-OH Busp and zolmitriptan in the 6-OHDA rat model.

Animals: 67 Sprague-Dawley male rats (bred in house, originally from SLAC Laboratory Animal Co. Ltd) at 9-week of age at body weight of 200 to 250 g from Shanghai SLAC Co. Ltd. arrive at the laboratory at least 1 week prior to behavioural testing. Rats are housed in groups of n=2/cage. Animals have ad libitum access to standard rodent chow and water. Animal housing and testing rooms are maintained under controlled environmental conditions and within close proximity of each other. Animal housing rooms are on a 12-hour light-dark cycle with lights on at 6:00 AM and maintained at 70° F./21° C. (range: 68-72° F./20-22° C.) with a humidity range of 20-40%. Test rooms are maintained at 68-72° F. with a humidity range of 20-40%.

6-OHDA lesion surgery: Dopamine (DA)-denervating lesions are performed by unilateral injection of 6-OHDA in the ascending nigrostriatal pathway as detailed in Example I. After recovery from surgery, rats with nearly complete (>90%) lesions are selected by means of an apomorphin-induced rotation test. I.p. injection of 0.5 mg/kg apomorphine•HCl (Sigma) in saline evokes contralateral turning, which is considered to be the result of de-nervated hypersensitivity of DA receptors in the lesion side. Rotational behaviour in response to DA agonists grossly correlates with the severity of the lesion. Quantification of the rotational response is accomplished in rats by counting the turns in 30 minutes. Rats with rotational score ≥6 turns/min are selected for next tests. Animals are then allocated into two well-matched sub-groups (according to the amphetamine rotation) and receive daily treatment as described below.

Drugs and treatment regimens: L-DOPA methyl ester combined with benserazide HCl is administered as detailed in Example I.

L-DOPA Induced AIMs and Drugs Screening Test

Rats are tested for AIMs as described above in Example I. To determine the effects of specific doses of buspirone and 6-OH-Busp, and a combination of 6-OH-Busp and fenobam the following group setting was used:
1. L-DOPA 6 mg/kg (20 min before test); Vehicle: (10% tween80, i.p., 30 min before test, n=8)
2. L-DOPA 6 mg/kg (20 min before test); buspirone (1 mg/kg, i.p., 30 min before test, n=8)
3. L-DOPA 6 mg/kg (20 min before test); 6-OH-Busp (1 mg/kg, i.p., 30 min before test, n=8)
4. L-DOPA 6 mg/kg (20 min before test); 6-OH-Busp (5 mg/kg, i.p., 30 min before test, n=8)
5. L-DOPA 6 mg/kg (20 min before test); 6-OH-Busp (1 mg/kg, i.p., 30 min before test, n=8)+fenobam (10 mg/kg, i.p., 30 min before test, n=8)
6. L-DOPA 6 mg/kg (20 min before test); 6-OH-Busp (5 mg/kg, i.p., 30 min before test, n=8)+fenobam (10 mg/kg, i.p., 30 min before test, n=8)

The rats are allocated randomly to 5 groups, which are balanced with their total AIM score from the pre-screening test.

To determine the effects of a combination of 6-OH Busp and zolmitriptan the following group setting was used:
7. L-DOPA 6 mg/kg (20 min before test); 6-OH Busp (1 mg/kg, i.p., 30 min before test, n=8)+zolmitriptan (10 mg/kg, i.p., 30 min before test, n=8)
8. L-DOPA 6 mg/kg (20 min before test); 6-OH Busp (5 mg/kg, i.p., 30 min before test, n=8)+zolmitriptan (10 mg/kg, i.p., 30 min before test, n=8)

The results of the drug screening test can determine if 6-OH Busp, a combination of 6-OH Busp with fenobam, and/or a combination of 6-OH Busp with zolmitriptan, reduces AIMs and L-DOPA-induced dyskinesia.

Example III

The present study describes the evaluation of 6-OH-Busp and fenobam or zolmitriptan in the 6-OHDA rat model, administered simultaneously or sequentially.

Animals: 45 Sprague-Dawley male rats (bred in house, originally from SLAC Laboratory Animal Co. Ltd) at body weight of 390-535 g are housed in groups of n=2/cage. Animals have ad libitum access to standard rodent chow and water.

The dosing procedure is performed by appointed scientists who are not involved in the AIMs ratings. Fenobam is dosed 11 min, 2 h, and 5 h before AIMs ratings by s.c. injection individually according to the group setting. Zolmitriptan is dosed 11 min, 2 h, and 5 h before AIMs ratings by s.c. injection individually according to the group setting. 6-OH-Busp is dosed 11 min before AIMs ratings by s.c. injection. The mixture of L-DOPA (8 mg/kg) and benserazide (15 mg/kg) is dosed 10 min before AIMs ratings. S.c. injections are on each sides of the back of the rats.

AIMs ratings are performed as detailed in Example I. For each rat, a score is given to each AIMs subtype (Lo, Li, Ax and OI) at each time point. The total AIMs are summed from scores of Li, Ax and OI in each time point. The total AIMs sum is calculated by summing the total AIMs of all time points. Data is expressed as mean±SEM and analysed with one way ANOVA followed by post hoc Newman-Keuls tests or unpaired t tests. Data is analyzed and graphed by Graph Pad Prism 5.

Example IV

The present study describes the evaluation of zonizamide, rizatriptan and 6-OH-Busp in the 6-OHDA rat model as described in Example I & II.
L-DOPA Induced AIMs and Drugs Screening Test
Rats are tested for AIMs as described above in Example I. To determine the effects of time of administration of combinations of 6-OH-Busp and zonizamide or rizatriptan the following group setting is used:
1. L-DOPA (6 mg/kg, s.c., 20 min before test); Vehicle: (10% tween80, s.c., 25 min before test, n=6).
2. L-DOPA (6 mg/kg, s.c., 20 min before test); 6-OH-Busp (1 mg/kg, s.c., 25 min before test, n=6)+zonizamide (3 mg/kg, s.c., 45 min before test, n=6).
3. L-DOPA (6 mg/kg, s.c., 20 min before test); 6-OH-Busp (1 mg/kg, s.c., 25 min before test, n=6)+zonizamide (3 mg/kg, s.c., 60 min before test, n=6).
4. L-DOPA (6 mg/kg, s.c., 20 min before test); 6-OH-Busp (1 mg/kg, s.c., 25 min before test, n=6)+zonizamide (3 mg/kg, s.c., 25 min before test, n=6).
5. L-DOPA (6 mg/kg, s.c., 20 min before test); 6-OH Busp (1 mg/kg, s.c., 25 min before test, n=6)+rizatriptan (3 mg/kg, s.c., 45 min before test, n=6).
6. L-DOPA (6 mg/kg, s.c., 20 min before test); 6-OH Busp (1 mg/kg, s.c., 25 min before test, n=6)+rizatriptan (3 mg/kg, s.c., 60 min before test, n=6).
7. L-DOPA (6 mg/kg, s.c., 20 min before test); 6-OH Busp (1 mg/kg, s.c., 25 min before test, n=6)+rizatriptan (3 mg/kg, s.c., 25 min before test, n=6).
The rats are allocated randomly to 4 groups, which are balanced with their total AIM score from pre-screening test.
The results of the drug screening test can determine if 6-OH-Busp in combination with zonizamide or rizatriptan reduces L-DOPA-induced dyskinesia.

Example V

The present study describes the evaluation of topiramate and 6-OH-Busp, and zolmitriptan and 6-OH-Busp, in the 6-OHDA rat model as described in Example I & II.
L-DOPA Induced AIMs and Drugs Screening Test
Rats are tested for AIMs as described above in Example I.
To determine the effects of time of administration of combinations of 6-OH-Busp and topiramate; or combinations of 6-OH-Busp and zolmitriptan; the following group setting is used:
1. L-DOPA 6 mg/kg+15 mg/kg benserazide, s.c. 10 min before test;
2. 6-OH Busp 1 mg/kg, s.c.; L-DOPA 6 mg/kg+15 mg/kg benserazide, sc; all compounds 10 min before test.
3. 6-OH Busp 1 mg/kg, s.c.+topiramate 10 mg/kg, s.c.; L-DOPA 6 mg/kg+15 mg/kg benserazide, s.c.; all compounds 10 min before test.
4. topiramate 3 mg/kg, s.c., 2 hr before test+6-OH Busp 1 mg/kg, s.c., 10 min before test; L-DOPA 6 mg/kg+15 mg/kg benserazide, s.c.; 10 min before test.
5. 6-OH Busp 1 mg/kg, s.c.+zolmitriptan 10 mg/kg, s.c.; L-DOPA 6 mg/kg+15 mg/kg benserazide, s.c.; all compounds 10 min before test.
6. zolmitriptan 3 mg/kg, s.c., 2 hr before test+6-OH Busp 1 mg/kg, s.c., 10 min before test; L-DOPA 6 mg/kg+15 mg/kg benserazide, s.c.; 10 min before test.
The rats are allocated randomly to 4 groups, which are balanced with their total AIM score from pre-screening test.
The results of the drug screening test 1-4. can determine if topiramate in combination with 6-OH Busp reduces L-DOPA-induced dyskinesia, and if topiramate administered before 6-OH Busp further reduces AIMs.
The results of the drug screening test 1, 2, 5 and 6 can determine if zolmitriptan in combination with 6-OH Busp reduces L-DOPA-induced dyskinesia, and if zolmitriptan administered before 6-OH Busp further reduces AIMs.

Example VI

The plasma concentrations as a function of time after administration of the drugs of the present invention can be determined by pharmacokinetic studies.
Male Sprague-Dawley rats (200-300 g) are used for the pharmacokinetic studies, following acclimatization for 5 days after arrival.
i) 6-OH-Busp (0.04 mg/mL) and fenobam (2.0 mg/mL) are dissolved in separate formulations consisting of aqueous 10% hydroxyl-propyl beta cyclodextrin, pH 6. fenobam (10 mg/kg) is administered s.c. to the rats at time 0 min and 6-OH-Busp (0.2 mg/kg) is subsequently dosed s.c. at time 30 min.
ii) 6-OH Busp (0.04 mg/mL) and zolmitriptan (2.0 mg/mL) are dissolved in separate formulations consisting of aqueous 10% hydroxyl-propyl beta cyclodextrin, pH 6. zolmitriptan (10 mg/kg) is administered s.c. to the rats at time 0 min and 6-OH-Busp (0.2 mg/kg) is subsequently dosed s.c. at time 30 min.
Plasma concentration-time profiles of 6-OH-Busp and fenobam, or 6-OH-Busp and zolmitriptan, are determined from blood samples drawn serially from a catheter surgically implanted in the carotid artery in rats. Following administration of fenobam or zolmitriptan, 9 serial blood samples (~200 µL) are taken from each rat at time 10, 20, 30, 45, 60, 120, 180, 240, 360 min.
Blood samples are collected in EDTA-coated tubes and centrifuged for 10 min at 4° C. after which plasma is transferred to fresh vials and stored at −80° C.
Quantification of 6-OH-Busp and fenobam or zolmitriptan is performed with liquid chromatography, tandem mass spectrometry (LC-MS/MS). A standard curve consists of 8 calibration standards (1-500 ng/ml for 6-OH-Busp and 1-3000 ng/ml for fenobam or zolmitriptan, respectively) for the LC-MS/MS method used for quantification.

Example VII

The Present Study Describes the Evaluation of a Combination of 6-OH-Busp and Fenobam or Zolmitriptan in the Stepping Test for Effects on Symptoms of Parkinson's Disease The stepping test (Schallert et al., 1992) is performed as described by Kirik et al., 2001 with little modifications. Briefly, the rat is held by the experimenter fixing its hindlimbs with one hand and the forelimb not to be monitored with the other, while the unrestrained forepaw is touching the table. The number of adjusting steps is counted, while the rat is moved sideways along the table surface (90 cm in 5 s), in the forehand and backhand direction, for both forelimbs, and the average of the steps in the two directions is considered. Performance of the animals in the stepping test is assessed during treatment period 1 (after training sessions and reach of a stable performance) in the L-DOPA, 6-OH-Busp and fenobam- or zolmitriptan-treated group, and in a group of naive rats, after administration of L-DOPA, 6-OH-Busp and fenobam or zolmitriptan+ or L-DOPA only, respectively. On the day of the test (day 5 of treatment period 1) L-DOPA, 6-OH-Busp and fenobam- or zolmitriptan-treated and naïve rats are tested twice in baseline condition and two more times 60 min after administration of the drugs. Values are reported as an average of the two sessions on and off drug. The present study can determine if 6-OH-Busp (1 mg/kg s.c.) in combination with fenobam (10 mg/kg s.s., which significantly reduce L-DOPA induced dyskinesia) or zolmitriptan (10 mg/kg i.p., which significantly reduce L-DOPA induced dyskinesia) will impair the ability of L-DOPA to improve motor function.

Example VIII

The Present Study Describes the Evaluation of a Combination of 6-OH-Busp and Fenobam or Zolmitriptan in the VCM Test for Effects on Tardive Dyskinesia The chronic vacuous chewing movement model (VCM model) for TD dyskinesia is established following the procedures described by Meaghan C. Creed et al. (The Journal of Neuroscience, 2012; 32(28): 9574-9581).

In brief; 110 male SD rats (200~220 g) are treated with haloperidol (decanoate; 21 mg/kg i.m once every 3 weeks throughout the entire study to induce and maintain the VCMs. After 12 weeks the haloperidol-induced VCMs are rated. For each VCM assessment, the rat is placed in a quiet box and allowed to acclimate for 10 min. VCMs counts for each rat is recorded for 5 min. The rating is performed each week for 3 consecutive weeks (once per week). VCMs are defined as jaw movements in the vertical plane not directed at specific objects accompanied or not by tongue protrusions. Discrete bursts of jaw tremors are counted as one VCM. The count is stopped whenever grooming begin and will restart when grooming stop. The count of VCMs during 5 min is recorded for each rat. Data is analyzed and graphed by GraphPad Prism 6. The rats with VCMs counts ≥18 per 5 min among three consecutive testing weeks are used for compound tests.

For compound tests the dosing procedure is performed by appointed scientists who are not involved in the VCMs ratings. Haloperidol (1 mg/kg) is dosed 30 min before VCMs ratings. Drugs are dosed 0.5 min after haloperidol dosing by s.c. injection individually according to the group setting. S.c. injections are on each sides of the back of the rats. VCMs ratings are performed in a quiet room by well-trained observers who are experimentally blind to the pharmacological treatment conditions.

To determine the effects of specific doses of 6-OH-Busp, and a combination of 6-OH-Busp and fenobam (all compounds are given s.c.) the following group setting is used:
1. Haloperidol (1 mg/kg); Vehicle: (10% tween80, n=8)
2. Haloperidol (1 mg/kg); fenobam (10 mg/kg, n=8)
3. Haloperidol (1 mg/kg); 6-OH-Busp (1 mg/kg, n=8)
4. Haloperidol (1 mg/kg); 6-OH-Busp (5 mg/kg, n=8)
5. Haloperidol (1 mg/kg); 6-OH-Busp (1 mg/kg, n=8)+ fenobam (10 mg/kg, n=8)
6. Haloperidol (1 mg/kg); 6-OH-Busp (5 mg/kg, n=8)+ fenobam (10 mg/kg, n=8)

To determine the effects of specific doses of 6-OH-Busp, and a combination of 6-OH-Busp and zolmitriptan the following group setting is used:
1. Haloperidol (1 mg/kg); Vehicle: (10% tween80, i.p., n=8)
2. Haloperidol (1 mg/kg); zolmitriptan (10 mg/kg, i.p., i.p., n=8)
3. Haloperidol (1 mg/kg); 6-OH-Busp (1 mg/kg, i.p., n=8)
4. Haloperidol (1 mg/kg); 6-OH-Busp (5 mg/kg, i.p., n=8)
5. Haloperidol (1 mg/kg); 6-OH-Busp (1 mg/kg, i.p., n=8)+ zolmitriptan (10 mg/kg, i.p., i.p., n=8)
6. Haloperidol (1 mg/kg); 6-OH-Busp (5 mg/kg, i.p., n=8)+ zolmitriptan (10 mg/kg, i.p., i.p., n=8)

The rats are allocated randomly to 5 groups, which are balanced with their total AIM score from the pre-screening test.

The present study can determine if 6-OH-Busp in combination with fenobam or zolmitriptan reduces haloperidol induced tardive dyskinesia in the rat VCM model.

Example IX

The Present Study Describes the Evaluation of a Combination of 6-OH-Busp and Topiramate or Rizatriptan in the VCM Test for Effects on Tardive Dyskinesia The VCM model for TD dyskinesia is established as described in Example VIII.

To determine the effects of specific doses of 6-OH-Busp, and a combination of 6-OH-Busp and topiramate, the following group setting is used:
1. Haloperidol (1 mg/kg); Vehicle: (10% tween80, i.p., n=8)
2. Haloperidol (1 mg/kg); topiramate (10 mg/kg, i.p., n=8)
3. Haloperidol (1 mg/kg); 6-OH-Busp (1 mg/kg, i.p., n=8)
4. Haloperidol (1 mg/kg); 6-OH-Busp (5 mg/kg, i.p., n=8)
5. Haloperidol (1 mg/kg); 6-OH-Busp (1 mg/kg, i.p., n=8)+ topiramate (3 mg/kg, i.p., n=8)
6. Haloperidol (1 mg/kg); 6-OH-Busp (1 mg/kg, i.p., n=8)+ topiramate (10 mg/kg, i.p., n=8)

To determine the effects of specific doses of 6-OH-Busp, and a combination of 6-OH-Busp and rizatriptan the following group setting is used:
1. Haloperidol (1 mg/kg); Vehicle: (10% tween80, i.p., n=8)
2. Haloperidol (1 mg/kg); rizatriptan (3 mg/kg, s.c., n=8)
3. Haloperidol (1 mg/kg); 6-OH-Busp (1 mg/kg, i.p., n=8)
4. Haloperidol (1 mg/kg); 6-OH-Busp (5 mg/kg, i.p., n=8)
5. Haloperidol (1 mg/kg); 6-OH-Busp (1 mg/kg, i.p., n=8)+ rizatriptan (3 mg/kg, s.c., n=8)
6. Haloperidol (1 mg/kg); 6-OH-Busp (1 mg/kg, i.p., n=8)+ rizatriptan (3 mg/kg, s.c., n=8)

The rats are allocated randomly to 4 groups, which are balanced with their total AIM score from pre-screening test.

The present study can determine if 6-OH-Busp in combination with topiramate or rizatriptan reduces haloperidol induced tardive dyskinesia in the rat VCM model.

Example X

The Present Study Describes the Evaluation of a Combination of 6-OH-Busp and Fenobam or Zolmitriptan in the Reserpine Test for Effects on Tardive Dyskinesia Fenobam or zolmitriptan given in combination with 6-OH-Busp is evaluated for activity against reserpine-induced tardive dyskinesia in mice. Reserpine (1 mg/kg) is injected subcutaneously s.c. to induce tardive dyskinesia on days 1 and 3. Combinations of fenobam with 6-OH-Busp are given s.c. 24 hours following the 2nd reserpine injection; or combinations of zolmitriptan with 6-OH-Busp are given intraperitoneally (i.p.) 24 hours following the 2nd reserpine injection. VCM (vacuous chewing movements) are measured for 10 minutes, 1 hour after the 2nd injection of test compounds on day 4. 6-OH-Busp and fenobam or zolmitriptan dissolved/suspended in 20% Tween 20/0.9% NaCl are administered intraperitoneally with a dosing volume of 10 mL/kg. All the test substances are prepared freshly before use.

Male ICR mice weighing 36±2 g are housed in animal cages with a space allocation of 29×18×13 cm for 5 mice. All animals are maintained in a hygienic environment under controlled temperature (20° C.-24° C.), humidity (50%-80%) with 12 hours light/dark cycles for at least three days prior to use. Free access to standard lab and tap water is granted. All aspects of this work including housing, experimentation and disposal of animals are performed in general accordance with the Guide for the Care and Use of Laboratory Animals (National Academy Press, Washington, D.C., 1996).

Groups of 10 male ICR mice weighing 36±2 g (at arrival) are used. All animals are challenged with 1st dose of reserpine (1 mg/kg s.c.) on day 1, followed by 2nd dosing of reserpine separated by 48 hours on day 3 to induce tardive dyskinesia. Vehicle and test articles are injected intraperitoneally 24 hours after the 2nd challenge of reserpine on day 4. One hour after dosing of the 2nd article, behavioural observations are carried out for vacuous chewing movements.

For the behavioural assessment, animals are individually placed in a plexiglass cage (13 cm×23 cm×13 cm). Mirrors were placed under the floor of the cage to permit observation of oral movements when the animals faced away from the observer. After a 5 min period of habituation, the occurrence of vacuous chewing movements (VCM) is counted for a further 10 min period. VCM are referred to as single mouth openings in the vertical plane not directed toward physical material. If VCM occurred during a period of grooming, they are not taken into account.

The total number of VCM each group is recorded and the mean±SEM for each group was determined. One-way ANOVA followed by Dunnett's test is applied for comparison between vehicle control and treated groups. Differences are considered significant at P<0.05 (*).

The present study can determine if 6-OH-Busp in combination with fenobam or zolmitriptan reduces reserpine induced tardive dyskinesia in mice.

Example XI (Model Creation)

The 6-OHDA rat model as described below is useful for evaluation of buspirone metabolites for treatment of movement disorders associated with Parkinson's disease and LID.

The 6-OHDA Rat Model

6-OHDA (6-hydroxydopamine) is a neurotoxin that selectively kills dopaminergic and noradrenergic neurons and induces a reduction of dopamine levels in the brain. Administration of L-DOPA to unilaterally 6-OHDA-lesioned rats induces abnormal involuntary movements (AIMs). These are axial, limb and oral movements that occur only on the body side that is ipsilateral to the lesion. AIM rat models have been shown useful because they respond to a number of drugs which have been shown to suppress dyskinesia (including PD) in humans.

Test Procedure:

Animals: 80 experimentally-naïve, male, 9 weeks old Sprague-Dawley rats at body weight of 200 to 250 g arrive at the laboratory at least 1 week prior to behavioural testing. Rats were housed in groups of n=2/cage. Animals had ad libitum access to standard rodent chow and water. Animal housing and testing rooms were maintained under controlled environmental conditions and were within close proximity of each other. Animal housing rooms were on a 12-hour light-dark cycle with lights on at 6:00 AM and maintained at 70° F./21° C. (range: 68-72° F./20-22° C.) with a humidity range of 20-40%. Testing rooms were maintained at 68-72° F. with a humidity range of 20-40%. DA (dopamine)-denervating lesions were performed by unilateral injection of 6-OHDA in the ascending nigrostriatal pathway. Rats were anesthetized with pentobarbital sodium 40 mg/kg (i.p.) and positioned in a stereotactic frame. 6-OHDA was injected into the right ascending DA bundle at the following coordinates relative to bregma and dural surface: A (anterior-posterior), L (lateral), V (dorsoventral): A −1.8, L −2.0, V −8.6, tooth bar 0.0.

The neurotoxin injections were performed at a rate of 1 ul/min, and the injection cannula is left in place for an additional 2-3 min thereafter. Two weeks after surgery, contralateral full body turns were recorded over 30 min, following s.c. injection of 0.5 mg/kg of apomorphine sulfate. The animals were placed in plastic Perspex bowls (30 cm in diameter) and the rotational behavior (360° turns) is recorded by an automated rotometer for 90 min after the s.c. injection of 0.5 mg/kg of apomorphine sulfate. Apomorphine (0.5 mg/kg, s.c.) induced contralateral rotation in unilateral 6-OHDA lesioned rats. 73 rats with rotations ≥180/30 min, indicating >90% DA lesion in nigrostriatal pathway, were chosen as the PD model rats for chronic L-DOPA treatment.

Drugs and Treatment Regimens

Drug Treatment:

Starting one day after the apomorphine-induced rotation test, 6-OHDA-lesioned rats were treated with daily L-DOPA (Sigma-Aldrich, Germany) (8 mg/kg plus benserazide 15 mg/kg, s.c.) for 21 days. Rats were placed individually in transparent plastic cages without bedding material and scored every 20 min following the injection of L-DOPA for the entire time course of dyskinesias (120 min). The AIMs were classified into four subtypes according to their topographic distributions such as Locomotive, Forelimb, Axial and Orolingual behaviors. The severity of each AIM subtype was assessed by using scores from 0 to 4 (1: occasional, i.e. present less than 50% of the time; 2: frequent, i.e. present more than 50% of the time; 3: continuous, but interrupted by strong sensory stimuli; 4: continuous, not interrupted by strong sensory stimuli). In this study, rats with an AIMs≥28 were considered highly dyskinetic, while rats with an AIMs<28 either low or none-dyskinetic.

After chronic L-DOPA treatment on PD rats for 21 days, 42 LID model rats (348 g~501 g, 15 weeks old) were successfully created with the criteria of total AIM scores (Lo+Li+AX+OI)≥28 points.

L-DOPA Induced AIMs and Drugs Screening Test

AIMs ratings were performed by an investigator who was kept unaware of the pharmacological treatment administered to each rat (experimentally blinded). In order to quantify the severity of the AIMs, rats were observed individually in their standard cages every 20th minute at 20-180 min after an injection of l-DOPA. The AIM's were classified into four subtypes:

(A) axial AIMs, i.e., dystonic or choreiform torsion of the trunk and neck towards the side contralateral to the lesion. In the mild cases: lateral flexion of the neck or torsional movements of the upper trunk towards the side contralateral to the lesion. With repeated injection of L-DOPA, this movement may develop into a pronounced and continuous dystonia-like axial torsion.

(B) limb AIMs, i.e., jerky and/or dystonic movements of the forelimb contralateral to the lesion. In mild cases: hyperkinetic, jerky stepping movements of the forelimb contralateral to the lesion, or small circular movements of the forelimb to and from the snout. As the severity of dyskinesia increases (which usually occurs with repeated administration of L-DOPA), the abnormal movements increase in amplitude, and assume mixed dystonic and hyperkinetic features. Dystonic movements are caused by sustained co-contraction of agonist/antagonist muscles; they are slow and force a body segment into unnatural positions. Hyperkinetic movements are fast and irregular in speed and direction. Sometimes the forelimb does not show jerky movements but becomes engaged in a continuous dystonic posture, which is also scored according to the time during which it is expressed.

(C) orolingual AIMs, i.e., twitching of orofacial muscles, and bursts of empty masticatory movements with protrusion of the tongue towards the side contralateral to the lesion. This form of dyskinesia affects facial, tongue, and masticatory muscles. It is recognizable as bursts of empty masticatory movements, accompanied to a variable degree by jaw opening, lateral translocations of the jaw, twitching of facial muscles, and protrusion of the tongue towards the side contralateral to the lesion. At its extreme severity, this subtype of dyskinesia engages all the above muscle groups with notable strength, and may also become complicated by self-mutilative biting on the skin of the forelimb contralateral to the lesion (easily recognizable by the fact that a round spot of skin becomes devoid of fur.

(D) locomotive AIMs, i.e., increased locomotion with contralateral side bias. The latter AIM subtype was recorded in conformity with the original description of the rat AIM scale, although it was later established that locomotive AIMs do not provide a specific measure of dyskinesia, but rather provide a correlate of contralateral turning behaviour in rodents with unilateral 6-OHDA lesions.

Each of the four subtypes are scored on a severity scale from 0 to 4, where 0=absent, 1=present during less than half of the observation time, 2=present for more than half of the observation time, 3=present all the time but suppressible by external stimuli, and 4=present all the time and not suppressible by external stimuli. Axial, limb and orolingual AIMs are found to be modulated in a similar way by all the tested substances.

Rats were tested for AIMs using the sum of locomotive (LO) oraxial (AX), limb (LI), and orolingual (OL) AIM scores per testing session for statistical analyses. The results showed the compounds that significantly reduce L-DOPA-induced dyskinesia.

Example XII

Figure 3:
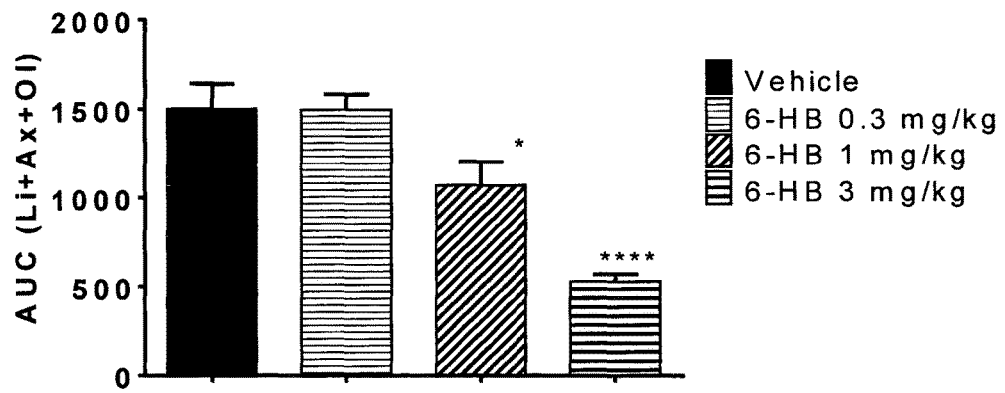
FIG. 3: Effects of 6-OH-Busp (6-HB) on AIMs measured as AUC from 10 min to 190 min after L-DOPA injection to dyskinestic rats. Data were expressed as Mean±SEM, ****$p<0.0001$, *$p<0.05$ vs. vehicle group, one way (See Example XII).

The present study evaluates the effects of buspirone and 6-OH Busp in the 6-OHDA rat model (FIG. 3).

AIMs baseline was tested on the 42 male LID model rats (362 g~510 g, 16 weeks of age) one day before compound test. Buspirone (1 mg/kg), 6-HB at three doses (0.3, 1 and 3 mg/kg) were dosed 11 min before AIMs ratings respectively. The mixture of L-DOPA (8 mg/kg) and Benserazide (15 mg/kg) was dosed 10 min before AIMs ratings. The dosing procedure was performed by appointed scientists who were not involved in the AIMs ratings. Test compounds or vehicle were dosed 11 min before AIMs ratings with s.c. injection. The L-DOPA (8 mg/kg)/Benserazide (15 mg/kg) mixture was dosed 10 min before AIMs ratings with s.c. injection. Sc injections were on each sides of the back of the rats.

AIMs ratings were performed in a quiet room by well-trained observers who were experimentally blind to the pharmacological treatment conditions. Rats were placed individually in transparent plastic cages without bedding material. Each rat was rated for 1 min every 20 min during the 190 min that follow the L-DOPA injection. The subtypes of AIMs were classified into four subtypes: (1) locomotive AIMs (Lo), i.e., increased locomotion with contralateral side bias; (2) limb AIMs (Li), i.e., jerky and/or dystonic movements of the forelimb contralateral to the lesion; (3) axial AIMs (Ax), i.e., dystonic or choreiform torsion of the trunk and neck towards the side contralateral to the lesion; (4) orolingual AIMs (Ol), i.e., twitching of orofacial muscles, and bursts of empty masticatory movements with protrusion of the tongue towards the side contralateral to the lesion. Each of the four subtypes was scored based on the duration and persistence of the dyskinetic behavior during the 1 min observation period. A rating scale of severity was from 0 to 4, where 0=absent, 1=present during less than half of the observation time, 2=present for more than half of the observation time, 3=present all the time but suppressible by external stimuli, and 4=present all the time and not suppressible by external stimuli.

Drugs and Treatment Regimens:
1. L-DOPA; Vehicle: (10% tween80, s.c.) (n=8)
2. L-DOPA; buspirone (1 mg/kg, s.c.) (n=8)
3. L-DOPA; 6-OH-Busp (0.3 mg/kg, s.c.) (n=8)
4. L-DOPA; 6-OH-Busp (1 mg/kg, s.c.), (n=9)
5. L-DOPA; 6-OH-Busp (3 mg/kg, s.c.), (n=9)

As positive control, buspirone (1 mg/kg s.c.) significantly attenuated total AIMs of LID rats at the time points of 50 min, 70 min, 90 min, 110 min, 130 min, 150 min, 170 min and 190 min, decreased the AUC of total AIMs from 10 min to 190 min compare to vehicle group.

At the time points of 30 min, 50 min, 70 min, 90 min, 110 min, 130 min, 150 min, 170 min and 190 min after L-DOPA injection, 6-OH-Busp dose-dependently decreased the AIMs of LID rats 6-OH-Busp dose-dependently decreased the total AIMs sum and AUC of total AIMs from 10 min to 190 min.

There were no obvious behavioral side effects found for all test compounds during the study period.

Example XIII

The purpose of this study was to evaluate the effects of combination of 6-OH-Busp and Zolmitriptan to attenuate the abnormal involuntary movements (AIMs) in L-DOPA induced dyskinesia (LID) model rats.

AIMs baseline was tested on the 42 male LID model rats (369 g~521 g, 17 weeks of age) one day before compound test. OH-Busp at two doses of 1 mg/kg and 3 mg/kg (s.c.), Zolmitriptan at the dose of 10 mg/kg (s.c.) and the mixture of 6-OH-Busp (1 mg/kg) and Zolmitriptan (10 mg/kg) were dosed 11 min before AIMs ratings respectively. The mixture of L-DOPA (8 mg/kg) and Benserazide (15 mg/kg) was dosed 10 min before AIMs ratings using s.c. dosing.

For each rat, a score was given to each AIMs subtype (Lo, Li, Ax and OI) at each time point. The total AIMs were summed from scores of Li, Ax and OI in each time point.

The total AIMs sum was calculated by summing the total AIMs of all time points. The AUC (area under curve) was calculated by a raw data plot of total AIMs (Li+Ax+OI) from 10 min to 130 min. Data were expressed as mean±SEM and analysed with one way ANOVA followed by post hoc Fisher's LSD tests. Data were analysed and graphed by Graph Pad Prism 6.

OH-Busp at the dose of 3 mg/kg significantly decreased the AIMs of LID rats at 50 min, 70 min, 90 min, 110 min, 130 min, 150 min, 170 min and 190 min.

When combined with Zolmitriptan (10 mg/kg), 6-OH-Busp at the dose of 1 mg/kg significantly attenuated the AIMs at the time points of 50 min, 70 min, 90 min, 110 min, 130 min, 150 min, 170 min and 190 min after L-DOPA injection as well as total AIMs sum when compared with vehicle group.

OH-Busp at the dose of 1 mg/kg did not significantly decrease the AIMs of LID rats at 50 min and 70 min after L-DOPA injection.

Zolmitriptan at 10 mg/kg s.c. did not have any effects on AIMs at any time points. Together this suggests that zolmitriptan was able to potentiate the effects of 6-OH-Busp on AIMs.

Example XIV

Figure 4:
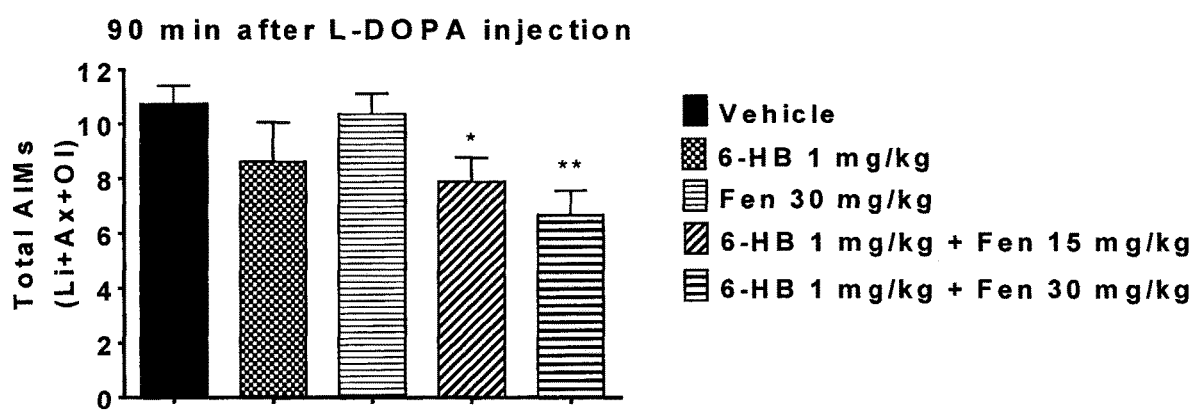
FIG. 4: Effects of 6-OH-Busp (6-HB) and fenobam (Fen) on AIMs measured at 90 min after L-DOPA injection to dyskinestic rats. Data were expressed as Mean±SEM, **$p<0.01$, *$p<0.05$ vs. vehicle group, one way ANOVA Fisher's LSD test, n=8~9 (See Example XIV).

The purpose of this study was to evaluate the effects of combination of 6-OH-Busp and Fenobam to attenuate the abnormal involuntary movements (AIMs) in L-DOPA induced dyskinesia (LID) model rats (FIG. 4).

AIMs baseline was tested on the 42 male LID model rats (380 g~560 g, 19 weeks of age) one day before compound test. Fenobam at two doses of 15 mg/kg i.p. and 30 mg/kg i.p. were dosed 20 min before AIMs ratings respectively. 6-OH-Busp at 1 mg/kg s.c. was dosed 11 min before AIMs ratings respectively. The mixture of L-DOPA (8 mg/kg) and Benserazide (15 mg/kg) was dosed 10 min before AIMs ratings with s.c. dosing.

For each rat, a score was given to each AIMs subtype (Lo, Li, Ax and OI) at each time point. The total AIMs were summed from scores of Li, Ax and OI in each time point. The total AIMs sum was calculated by summing the total AIMs of all time points. The AUC (area under curve) was calculated by a raw data plot of total AIMs (Li+Ax+OI) from 10 min to 130 min. Data were expressed as mean±SEM and analyzed with one way ANOVA followed by post hoc Fisher's LSD tests. Data were analyzed and graphed by Graph Pad Prism 6.

When combined with Fenobam (15 mg/kg or 30 mg/kg, i.p), 6-OH-Busp at the dose of 1 mg/kg significantly attenuated the AIMs at the time points of 90 min and 110 min after L-DOPA injection as well as total AIMs sum when compared with vehicle group. 6-OH-Busp at the dose of 1 mg/kg at 90 min and 110 min after L-DOPA injection after L-DOPA injection did not have significant effects on the AIMs of LID rats.

Fenobam (30 mg/kg, s.c.) did not have significant effects on AIMs of LID rats at any time points.

There were no obvious behavioral side effects found for all test compounds during the study period.

Example XV

The Present Study Describes the Evaluation of 6-OH-Busp in the Stepping Test for Effects on Symptoms of Parkinson's Disease The stepping test (Schallert et al., 1992) was performed as described by Kirik et al., 2001 with little modifications. Briefly, the rat was held by the experimenter fixing its hindlimbs with one hand and the forelimb not to be monitored with the other, while the unrestrained forepaw was touching the table. The number of adjusting steps was counted, while the rat was moved sideways along the table surface (90 cm in 5 s), in the forehand and backhand direction, for both forelimbs, and the average of the steps in the two directions is considered.

30 male PD model rats were used for adjusting steps test with the following groups:
1. Vehicle 1+Vehicle 2 (n=7)
2. Vehicle 1+L-DOPA (10 mg/kg, sc) (n=7)
3. 6-OH-Busp (3 mg/kg, sc)+Vehicle 2 (n=8)
4. 6-OH-Busp (3 mg/kg, sc)+L-DOPA (10 mg/kg, sc)

The PD rats were handled for 3 consecutive days. Vehicle 1 or 6-OH-Busp will s.c. dosed 61 min before adjusting steps test. Vehicle 2 or L-DOPA/Benserazide dosed 60 min before adjusting steps test. On testing day, the rats were held by both hind limbs and the untested forepaw. The test forepaw was placed on a flat surface and dragged in the forehand direction for 90 cm distance over 5 s. The number of adjusting steps was counted for both paws in the backhand and forehand directions of movement. The score for percent intact stepping was derived by taking the sum of the total steps with the lesioned forepaw dividing that number by total steps with the unlesioned forepaw and multiplying the outcome by 100. Data were analyzed and graphed by Graph Pad Prism 6.

The data show that L-DOPA (10 mg/kg, sc) increased the number of adjusting steps supporting an anti-Parkinson's disease effect. There was no significant different effect of adding 6-OH-Busp (3 mg/kg, sc) to L-DOPA (10 mg/kg, sc) suggesting that 6-OH-Busp does not impair L-DOPA efficacy.

The invention claimed is:

1. A method for treating L-DOPA induced dyskinesia (LID) or tardive dyskinesia, comprising:
    administering to a subject in need thereof a pharmaceutical composition comprising 6-hydroxybuspirone (6-OH-Busp) or a pharmaceutically acceptable salt or ester thereof,
    wherein said 6-OH-Busp is selected from the group consisting of the racemate of 6-OH-Busp, the S-form of 6-OH-Busp and the R-form of 6-OH-Busp.

2. The method of claim 1, wherein said 6-OH-Busp is the racemate of 6-OH-Busp.

3. The method of claim 1, wherein said subject is, or is to be, treated with a dopamine prodrug.

4. The method of claim 1, wherein said composition is a pharmaceutically acceptable composition.

5. The method of claim 1, wherein said composition further comprises a second active pharmaceutical ingredient, wherein the second active pharmaceutical ingredient is selected from the group consisting of:

a. an agonist of two or more of the 5-HT1B, 5-HT1D, and 5-HT1F receptors, wherein the agonist is a triptan;
b. a modulator of glutamate neurotransmission;
c. an NMDA receptor antagonist, an AMPA receptor antagonist, a kainite receptor antagonist, an AMPAR/kainite receptor antagonist, a mGluR Group 1 antagonist, a mGluR Group 2 agonist, and a mGluR Group 3 agonist;
d. an inhibitor of glutamate release; and
e. an ion-channel antagonist.

6. The method of claim 5, wherein said second active pharmaceutical ingredient is to be administered separately, sequentially or simultaneously from said pharmaceutical composition.

7. The method of claim 5, wherein the agonist of two or more of the 5-HT1B, 5-HT1D and 5-HT1F receptors is selected from the group consisting of zolmitriptan, rizatriptan, sumatriptan, naratriptan, almotriptan, frovatriptan, avitriptan, alniditan and eletriptan, or pharmaceutically acceptable derivatives thereof.

8. The method of claim 5, wherein the ion-channel antagonist is selected from the group consisting of a calcium channel antagonist, a T-Type calcium channel antagonist, an L-Type calcium channels antagonist, a $K^+$ channel antagonist and/or a $Na^+$ channel antagonist.

9. The method of claim 5, wherein said composition further comprises an additional active pharmaceutical ingredient which is a dopamine prodrug.

10. The method of claim 9, wherein said further active pharmaceutical ingredients are to be administered separately, sequentially or simultaneously from said pharmaceutical composition.

11. The method of claim 9, wherein said dopamine prodrug is L-DOPA.

\* \* \* \* \*